US010940306B2

(12) United States Patent
Truitt et al.

(10) Patent No.: US 10,940,306 B2
(45) Date of Patent: *Mar. 9, 2021

(54) CONNECTOR FOR TRANSFERRING FLUID AND METHOD OF USE

(71) Applicant: CareFusion 303, Inc., San Diego, CA (US)

(72) Inventors: Tim L. Truitt, Orange, CA (US); Alex Truman Mazza, Grand Terrace, CA (US); Cliff Colwell, Corona, CA (US); Jonathan Yeh, Diamond Bar, CA (US); Christopher J. Zollinger, Chino Hills, CA (US); Matthew Quach, San Gabriel, CA (US); George Michel Mansour, Pomona, CA (US)

(73) Assignee: CareFusion 303, Inc., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/684,407

(22) Filed: Nov. 14, 2019

(65) Prior Publication Data

US 2020/0078580 A1 Mar. 12, 2020

Related U.S. Application Data

(63) Continuation of application No. 15/623,301, filed on Jun. 14, 2017, now Pat. No. 10,478,607, which is a
(Continued)

(51) Int. Cl.
*A61M 39/10* (2006.01)
*F16K 15/14* (2006.01)
(Continued)

(52) U.S. Cl.
CPC .......... *A61M 39/105* (2013.01); *A61M 39/02* (2013.01); *A61M 39/0208* (2013.01);
(Continued)

(58) Field of Classification Search
CPC ............ A61M 39/105; A61M 39/0208; A61M 39/225; A61M 39/02; F16K 15/141; F16K 15/142; Y10T 137/0318
See application file for complete search history.

(56) References Cited

U.S. PATENT DOCUMENTS

| 4,141,379 A | 2/1979 | Manske |
| 4,246,932 A | 1/1981 | Raines |

(Continued)

FOREIGN PATENT DOCUMENTS

| CN | 1077654 | 10/1993 |
| CN | 1139010 | 1/1997 |

(Continued)

OTHER PUBLICATIONS

Australian Examination Report No. 1 for Application No. 2014228626, dated Aug. 4, 2017, 3 pages.
(Continued)

*Primary Examiner* — Kevin L Lee
(74) *Attorney, Agent, or Firm* — Morgan, Lewis & Bockius LLP

(57) ABSTRACT

A connector for transferring fluid and method therefor. The connector may have a first port and a second port which may be coupled together at a main channel with a valve element therein controlling fluid flow through the first port. The first port joins the main channel to provide a fluid path around the valve element and through the second port.

20 Claims, 14 Drawing Sheets

Related U.S. Application Data continuation-in-part of application No. 15/178,430, filed on Jun. 9, 2016, now Pat. No. 10,039,914, which is a continuation of application No. 14/172,766, filed on Feb. 4, 2014, now Pat. No. 9,393,398, which is a continuation-in-part of application No. 13/801,412, filed on Mar. 13, 2013, now abandoned, which is a continuation of application No. 13/039,956, filed on Mar. 3, 2011, now Pat. No. 8,640,725, which is a continuation of application No. 12/538,686, filed on Aug. 10, 2009, now Pat. No. 7,909,056, which is a continuation of application No. 10/914,797, filed on Aug. 9, 2004, now Pat. No. 7,600,530.

(51) Int. Cl.
*A61M 39/02* (2006.01)
*A61M 39/22* (2006.01)
*A61M 39/26* (2006.01)
*F16K 15/02* (2006.01)
*F16K 15/03* (2006.01)
*A61M 39/24* (2006.01)

(52) U.S. Cl.
CPC ......... *A61M 39/225* (2013.01); *F16K 15/141* (2013.01); *F16K 15/142* (2013.01); *A61M 39/24* (2013.01); *A61M 39/26* (2013.01); *F16K 15/023* (2013.01); *F16K 15/03* (2013.01); *Y10T 137/0318* (2015.04); *Y10T 137/7838* (2015.04); *Y10T 137/7842* (2015.04); *Y10T 137/7845* (2015.04); *Y10T 137/7879* (2015.04); *Y10T 137/86493* (2015.04); *Y10T 137/87571* (2015.04); *Y10T 137/87652* (2015.04); *Y10T 137/87684* (2015.04); *Y10T 137/9029* (2015.04)

(56) References Cited

U.S. PATENT DOCUMENTS

| | | | |
|---|---|---|---|
| 4,468,224 A | 8/1984 | Enzmann et al. | |
| 4,535,820 A | 8/1985 | Raines | |
| 4,654,031 A | 3/1987 | Lentz | |
| 4,666,429 A | 5/1987 | Stone | |
| 4,911,403 A | 3/1990 | Lockwood, Jr. | |
| 4,919,167 A | 4/1990 | Manska | |
| 5,092,857 A | 3/1992 | Fleischhacker | |
| 5,230,706 A | 7/1993 | Duquette | |
| 5,242,432 A | 9/1993 | DeFrank | |
| 5,300,034 A | 4/1994 | Behnke et al. | |
| 5,360,413 A | 11/1994 | Leason et al. | |
| 5,520,664 A | 5/1996 | Bricault, Jr. et al. | |
| 5,549,651 A | 8/1996 | Lynn | |
| 5,555,908 A | 9/1996 | Edwards et al. | |
| 5,623,969 A | 4/1997 | Raines | |
| 5,676,346 A | 10/1997 | Leinsing | |
| 5,690,612 A | 11/1997 | Lopez et al. | |
| 5,699,821 A | 12/1997 | Paradis | |
| 5,730,418 A | 3/1998 | Feith et al. | |
| 5,749,861 A | 5/1998 | Guala et al. | |
| 5,782,816 A | 7/1998 | Werschmidt et al. | |
| 5,992,462 A | 11/1999 | Atkinson et al. | |
| 6,024,729 A | 2/2000 | Dehdashtian et al. | |
| 6,050,978 A | 4/2000 | Orr et al. | |
| 6,245,048 B1 | 6/2001 | Fangrow, Jr. et al. | |
| 6,364,861 B1 | 4/2002 | Feith et al. | |
| 6,651,956 B2 | 11/2003 | Miller | |
| 6,679,219 B1 | 1/2004 | Pacinelli | |
| 6,886,803 B2 | 5/2005 | Mikiya et al. | |
| 7,160,272 B1 | 1/2007 | Eyal et al. | |
| 7,184,825 B2 | 2/2007 | Leinsing et al. | |
| 8,186,384 B2 | 5/2012 | Fujii et al. | |
| 8,257,320 B2 | 9/2012 | Feith et al. | |
| 8,291,936 B2 | 10/2012 | Carmody et al. | |
| 8,568,371 B2 | 10/2013 | Siopes et al. | |
| 8,640,725 B2 | 2/2014 | Truitt et al. | |
| 9,851,013 B2 | 12/2017 | Zhou et al. | |
| 10,039,914 B2 | 8/2018 | Truitt et al. | |
| 10,478,607 B2 * | 11/2019 | Truitt et al. | A61M 39/225 |
| 2002/0193752 A1 | 12/2002 | Lynn | |
| 2003/0050610 A1 | 3/2003 | Newton et al. | |
| 2003/0098430 A1 | 5/2003 | Leinsing et al. | |
| 2004/0227120 A1 | 11/2004 | Raybuck | |
| 2005/0059952 A1 | 3/2005 | Giuliano et al. | |
| 2005/0171489 A1 | 8/2005 | Weaver et al. | |
| 2005/0222541 A1 | 10/2005 | Lopez et al. | |
| 2006/0025724 A1 | 2/2006 | Chen | |
| 2006/0027270 A1 | 2/2006 | Truitt et al. | |
| 2006/0089603 A1 | 4/2006 | Truitt et al. | |
| 2006/0108554 A1 | 5/2006 | Enerson et al. | |
| 2006/0163515 A1 | 7/2006 | Ruschke | |
| 2006/0208210 A1 | 9/2006 | Raybuck | |
| 2007/0270756 A1 | 11/2007 | Peppel et al. | |
| 2008/0108956 A1 | 5/2008 | Lynn et al. | |
| 2009/0030401 A1 | 1/2009 | Phillips | |
| 2009/0057589 A1 | 3/2009 | Thorne, Jr. et al. | |
| 2009/0299300 A1 | 12/2009 | Truitt et al. | |
| 2010/0036330 A1 | 2/2010 | Plishka et al. | |
| 2010/0252768 A1 | 10/2010 | Caprera | |
| 2010/0256573 A1 | 10/2010 | Mansour et al. | |
| 2011/0028914 A1 | 2/2011 | Mansour et al. | |
| 2011/0028915 A1 | 2/2011 | Siopes et al. | |
| 2011/0046573 A1 | 2/2011 | Newton et al. | |
| 2011/0130724 A1 | 6/2011 | Mansour et al. | |
| 2011/0152787 A1 | 6/2011 | Truitt et al. | |
| 2012/0089086 A1 * | 4/2012 | Hokanson | A61M 39/045 604/70 |
| 2012/0310179 A1 | 12/2012 | Truitt et al. | |
| 2012/0316514 A1 | 12/2012 | Mansour | |
| 2013/0030386 A1 | 1/2013 | Panian et al. | |
| 2013/0190684 A1 | 7/2013 | Panian et al. | |
| 2014/0276466 A1 * | 9/2014 | Yeh et al. | A61M 39/26 604/256 |

FOREIGN PATENT DOCUMENTS

| | | |
|---|---|---|
| CN | 1305391 | 7/2001 |
| CN | 102481445 | 5/2012 |
| CN | 102497897 | 6/2012 |
| CN | 102686265 | 9/2012 |
| EP | 2075032 | 7/2009 |
| EP | 2719419 | 4/2014 |
| WO | WO-9826835 | 6/1998 |
| WO | WO-2004082756 | 9/2004 |
| WO | WO-2004/112866 | 12/2004 |
| WO | WO-2005011799 | 2/2005 |
| WO | WO-2006078355 | 7/2006 |
| WO | WO-2008091698 | 7/2008 |
| WO | WO-2011014265 | 2/2011 |
| WO | WO-2011060384 | 5/2011 |
| WO | WO-2013016077 | 1/2013 |
| WO | WO-2013099261 | 7/2013 |
| WO | WO-2013122148 | 8/2013 |

OTHER PUBLICATIONS

Chinese Office Action for Application No. 2014800143520, dated Dec. 5, 2016, 7 pages.
Chinese Office Action for Application No. 201480014557.9, dated Mar. 3, 2017, 6 pages excluding English translation.
Chinese Office Action for Application No. 201480014965.4, dated Mar. 3, 2017, 9 pages excluding English translation.
Chinese Office Action for Application No. 201480014971.X, dated Feb. 21, 2017, 6 pages excluding English translation.
Chinese Office Action for Application No. 201480015027.6, dated Mar. 10, 2017, 7 pages excluding English translation.
Chinese Office Action for Application No. 201480015065.1, dated Feb. 22, 2017, 7 pages excluding English translation.
Chinese Second Office Action for 201480014352.0, dated Jun. 21, 2017, 7 pages excluding translation.

(56) References Cited

OTHER PUBLICATIONS

European Office Action for Application No. 14/708451.1, dated Nov. 30, 2016, 3 pages.
European Office Action for Application No. 14158885.5, dated Dec. 16, 2015, 5 pages.
Extended European Search Reportand Written Opinion for Application No. 17158061.6, dated Jun. 20, 2017, 7 pages.
Extended European Search Report for Application No. 14778965.5, dated May 9, 2017, 13 pages.
Extended European Search Report in European Application No. 14158882.2 dated Jul. 7, 2014, 7 pages.
Extended European Search Report in European Application No. 14158885.5 dated May 12, 2014, 11 pages.
Extended European Search Report in European Application No. 14158891.3 dated Jul. 8, 2014, 6 pages.
Extended European Search Report in European Application No. 14158894.7 dated May 12, 2014, 8 pages.
Extended European Search Report in European Application No. 14158899.6 dated Jul. 8, 2014, 6 pages.
International Preliminary Report on Patentability for Application No. PCT/US2014/017486, dated Jul. 13, 2015, 21 pages.
International Search Report and Written Opinion in PCT Application No. PCT/US2014/017480 dated May 13, 2014, 13 pages.
International Search Report and Written Opinion in PCT Application No. PCT/US2014/017486 dated May 13, 2014, 14 pages.
International Search Report and Written Opinion in PCT Application No. PCT/US2014/017824 dated May 9, 2014, 21 pages.
International Search Report and Written Opinion in PCT Application No. PCT/US2014/017826 dated May 8, 2014, 10 pages.
International Search Report and Written Opinion in PCT Application No. PCT/US2014/017828 dated May 2, 2014, 10 pages.
International Search Report and Written Opinion in PCT Application No. PCT/US2014/023694 dated Jun. 26, 2014, 11 pages.
International Written Opinion of the International Preliminary Examining Authority for International Application No. PCT/US2014/017824, dated Mar. 23, 2015, 6 pages.
International Written Opinion of the International Preliminary Examining Authority for International Application No. PCT/US2014/017828, dated Mar. 20, 2015, 6 pages.
Partial Supplementary European Search Report for Application No. 14778965.5, dated Dec. 16, 2016, 7 pages excluding translation.

* cited by examiner

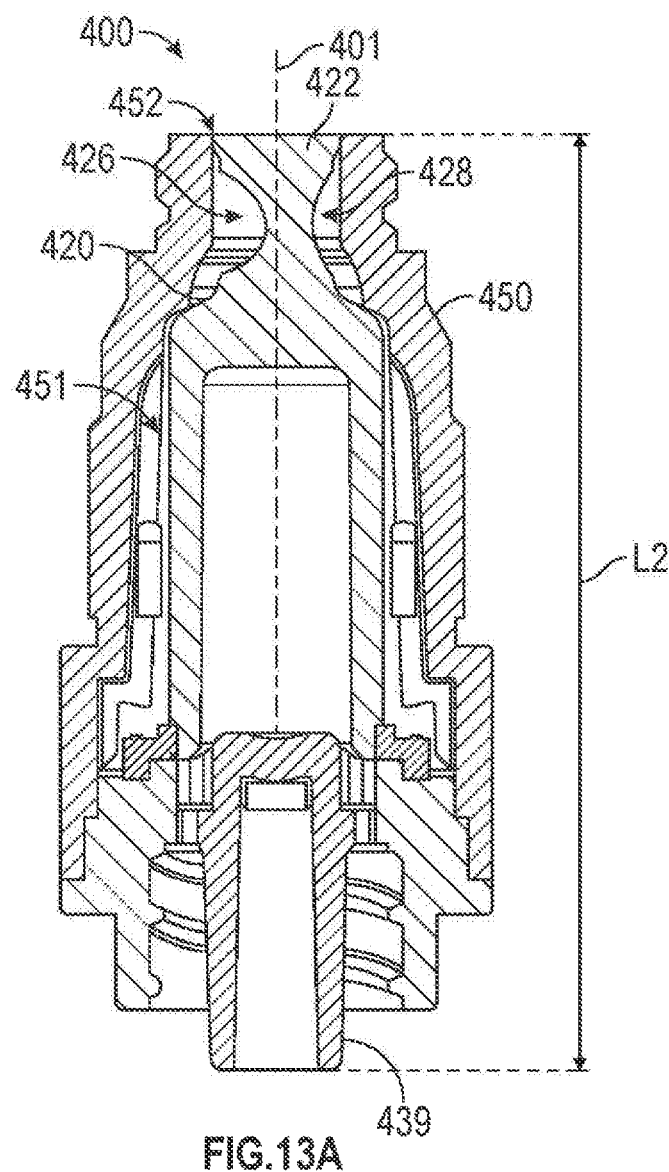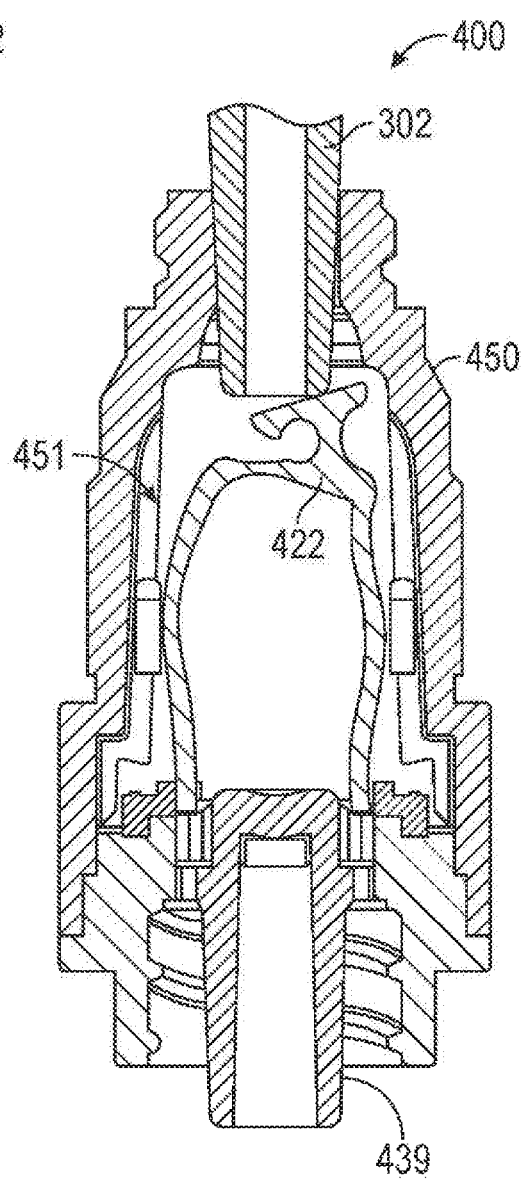
FIG.13A
FIG.13B

CONNECTOR FOR TRANSFERRING FLUID AND METHOD OF USE

CROSS-REFERENCE TO RELATED APPLICATIONS

This application is a continuation of U.S. application Ser. No. 15/623,301, filed Jun. 14, 2017, now U.S. Pat. No. 10,478,607, entitled "CONNECTOR FOR TRANSFERRING FLUID AND METHOD OF USE," which is a continuation-in-part of U.S. application Ser. No. 15/178,430, filed Jun. 9, 2016, now U.S. Pat. No. 10,039,914, entitled "CONNECTOR FOR TRANSFERRING FLUID AND METHOD OF USE," which is a continuation of U.S. application Ser. No. 14/172,766, filed Feb. 4, 2014, now U.S. Pat. No. 9,393,398, entitled "CONNECTOR FOR TRANSFERRING FLUID AND METHOD OF USE," which is a continuation of U.S. application Ser. No. 13/039,956, filed Mar. 3, 2011, now U.S. Pat. No. 8,640,725, entitled, "CONNECTOR FOR TRANSFERRING FLUID AND METHOD OF USE," which is a continuation of U.S. application Ser. No. 12/538,686, filed Aug. 10, 2009, now U.S. Pat. No. 7,909,056, entitled, "CONNECTOR FOR TRANSFERRING FLUID AND METHOD OF USE," which is a continuation of U.S. application Ser. No. 10/914,797, filed Aug. 9, 2004, now U.S. Pat. No. 7,600,530, entitled, "CONNECTOR WITH CHECK VALVE AND METHOD OF USE," and is a continuation-in-part of U.S. application Ser. No. 13/801,412, filed Mar. 13, 2013, now abandoned, entitled "NEEDLELESS CONNECTOR WITH FOLDING VALVE," the disclosure of each of which is incorporated herein by reference in its entirety for all purposes.

TECHNICAL FIELD

The present description is directed to a connector and method for transferring fluids and, in particular, a connector which incorporates a needleless access device to transfer fluid.

BACKGROUND OF THE INVENTION

Needless access devices are used to inject medications or other fluids into a patient or withdraw fluids from a patient. These devices have valves therein that are actuated, for example, by insertion of a male luer of a syringe into the device. The devices can include interconnectable male and female needleless connectors having a "Luer taper" conforming to an International Standards Organization (ISO) standard. The needleless access devices form part of an intravenous tubing set, which comprises a length of tubing, a primary needle or catheter, and/or other connectors. One end of a length of tubing is attached to the primary needle or catheter, which is stuck into a vein of the patient. The other end of the tubing can be connected to the needleless access device. Alternatively, the needleless access device can be connected directly to the primary needle or catheter. Such a configuration allows all injections/withdrawal of fluid to be made through the needleless access device. Thus, needless access devices eliminate the need for repeated needle sticks into the patient, thereby avoiding unnecessary trauma to the patient. In addition, needleless access devices prevent needle stick injuries and the possibility of transmitting blood borne pathogens to healthcare professionals.

Needless access devices can also take the form of a Y-connector having first and second inlet ports, an outlet port, and a valve located in the first inlet port. The outlet port of the Y-connector is connected by an intravenous tube to a primary needle or catheter, which is inserted into a patient. And, the second inlet port is connected via an intravenous tube to an intravenous bag. Such a configuration forms the main intravenous line. The first inlet port, which contains the valve, can be used to inject fluids and/or medication into the main intravenous line from a syringe or piggyback intravenous bag. Similar to other needleless access devices, the valve in the first inlet port of the Y-connector is actuated, for example, by insertion of a male luer of a syringe into the Y-connector.

Backflow check valves have also been used in medical connectors. Backflow check valves allow for flow of fluid in one direction while preventing flow of fluid in the other direction (i.e., backflow). For example, when a connector is placed along the path of fluid flow from an intravenous bag to a patient, the check valve acts as a one way valve, allowing fluid to flow to the patient while, at the same time, preventing fluid and/or blood from flowing away from the patient. Moreover, check valves have been used in Y-connectors, which have a first and second inlet port, and an outlet port. The check valve is located in the first inlet port and is positioned between, for example, an intravenous bag and the patient (i.e., the main intravenous line). The check valve allows fluid to flow from the intravenous bag to the patient. Additional fluids can be injected into the main intravenous line through the second inlet port. When fluid is injected into the second inlet port, the check valve blocks fluid from flowing around the check valve in a direction away from the patient and towards the intravenous bag.

BRIEF SUMMARY OF THE INVENTION

The present invention relates to a connector for transferring fluids. In particular, the connector of the present invention incorporates a needleless access device and a backflow check valve. The connector may comprise a housing having a first port, a second port, and a third port. A first valve element may be positioned in the first port and a second valve element may be positioned in the second port. A first fluid may flow between the first port and the third port. A second fluid may be introduced into the connector via the second port and can combine with the first fluid. Alternatively, the first fluid may be removed from the connector through the second port.

The present invention also relates to a method of transferring fluid. The first valve element may be in a first position in the first port as a first fluid flows between the first port and the third port. A fluid transfer device may be inserted into the second port to actuate the second valve element. Upon insertion of the fluid transfer device into the second port, the second valve element can move from a first position where the second port is closed (i.e., fluid cannot be injected into/withdrawn from the second port) to a second position where the second port is open (i.e., fluid can be injected into/withdrawn from the second port). And, when the fluid transfer device is removed from the second port, the second valve element may move from the opened position to the closed position. In the open position, a second fluid may be transferred between the fluid transfer device and the connector via the second port or the first fluid may be withdrawn from the connector. If a second fluid is transferred into the connector through the second port, the first valve element may move from the first position to a second position. In the second position, fluid may be prevented from flowing past the first valve element. Alternatively, if a first fluid is withdrawn from the connector through the second port, the first valve element may remain in the first position.

The foregoing has outlined rather broadly the features and technical advantages of the present invention in order that the detailed description of the invention that follows may be better understood. Additional features and advantages of the invention will be described hereinafter which form the subject of the claims of the invention. It should be appreciated by those skilled in the art that the conception and specific embodiment disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims. The novel features which are believed to be characteristic of the invention, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present invention.

BRIEF DESCRIPTION OF THE DRAWINGS

For a more complete understanding of the present invention, reference is now made to the following descriptions taken in conjunction with the accompanying drawings, in which:

FIGS. 13A and 13B are a cross-sectional view of an exemplary embodiment of the connector of the present invention.

DETAILED DESCRIPTION OF THE INVENTION

Figure 1:
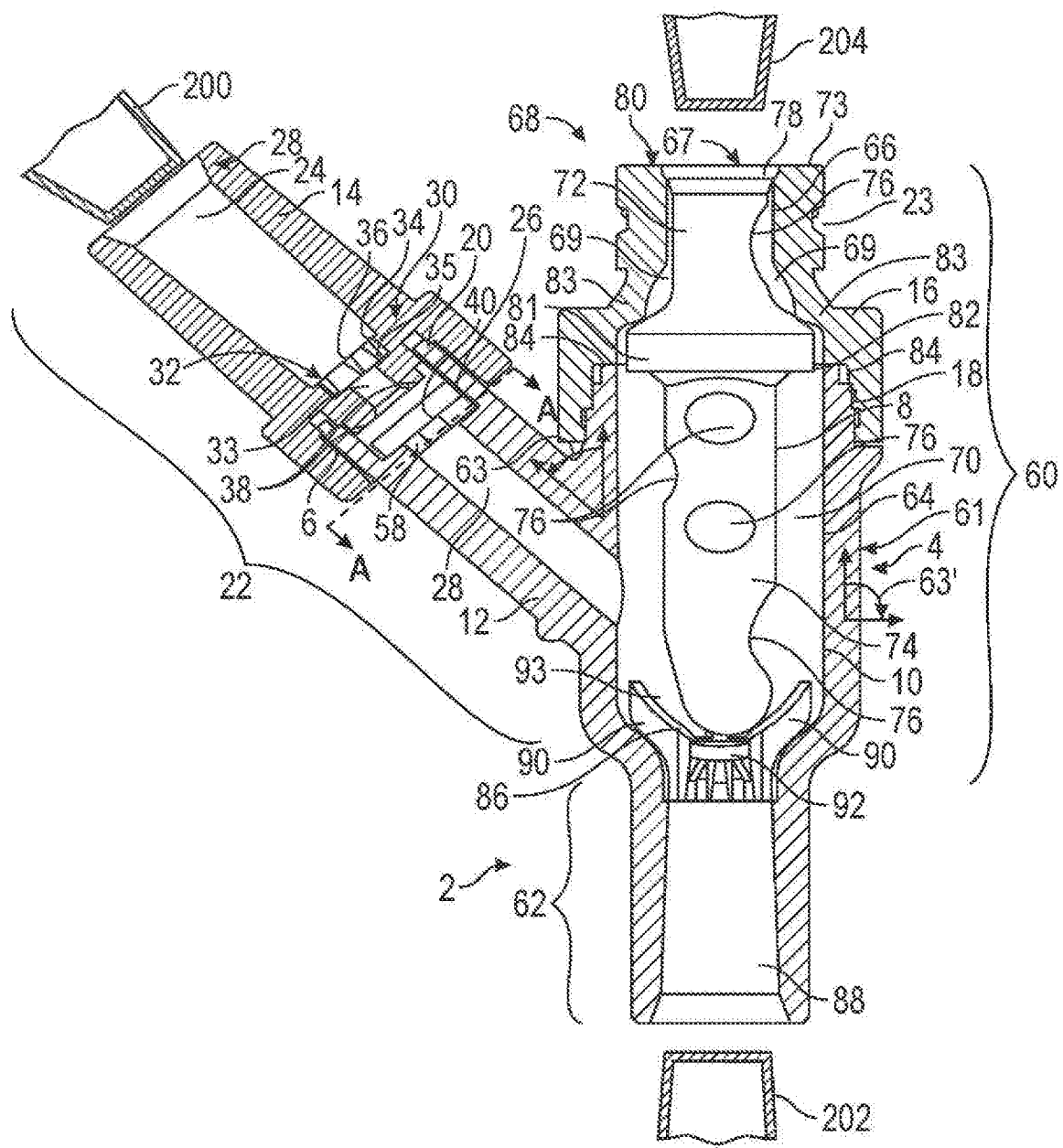
FIG. 1 is a partial cross-sectional view of an exemplary embodiment of the connector of the present invention.

FIG. 1 shows an exemplary embodiment of a connector 2 for transferring fluid. The term "fluid" may include, for example, blood, medication, saline, water, oxygen or other gas, air (i.e., a mixture of gases).

Figure 2:
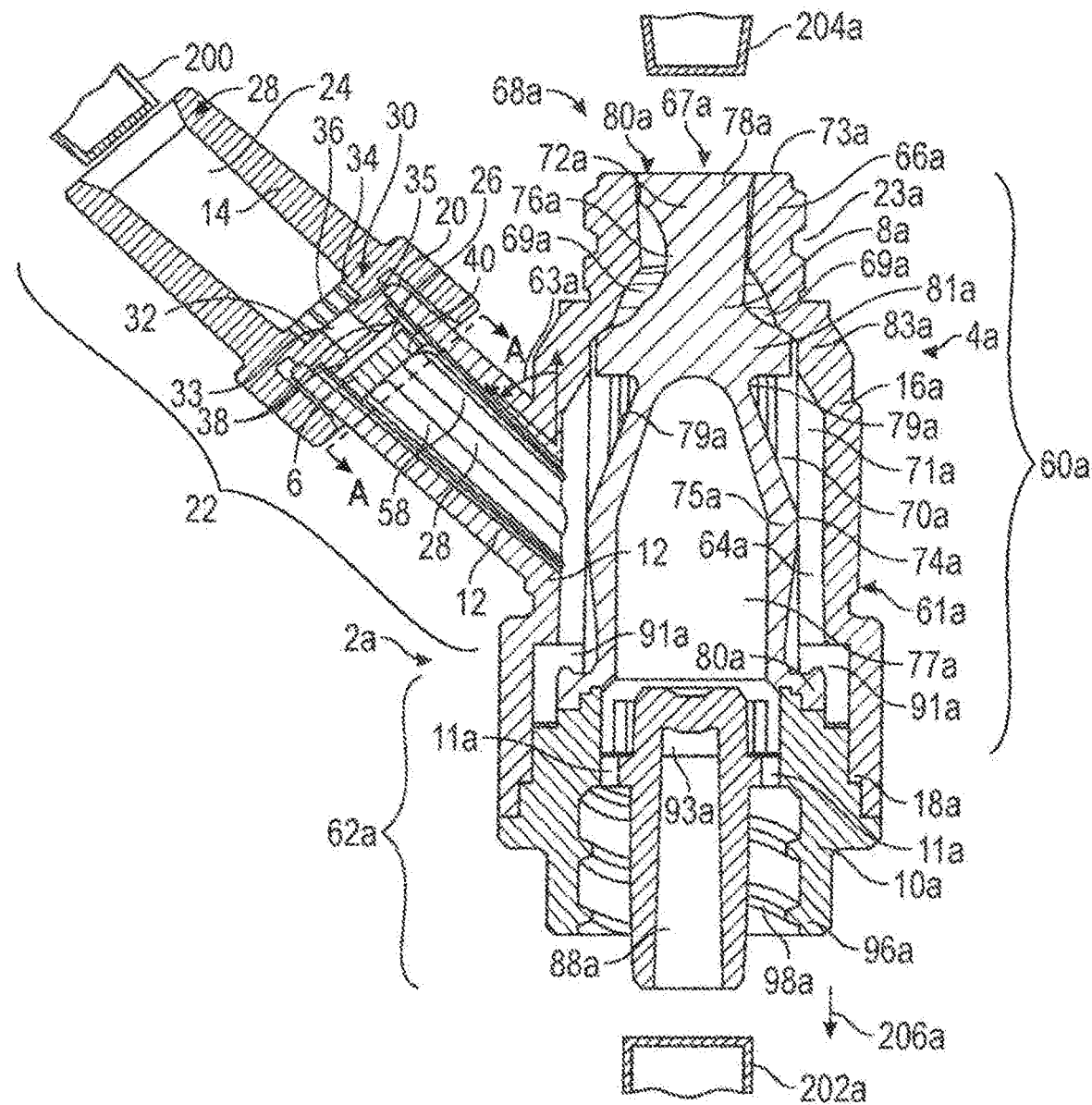
FIG. 2 is a cross-sectional view of an alternative exemplary embodiment of the connector of the present invention.

The connector 2 of the present invention may comprise a housing 4, a first valve element 6, and a second valve element 8. It should, however, be understood that those of ordinary skill in the art will recognize many modifications and substitutions which may be made to various elements of the present invention. The housing 4 may comprise a base portion 10, an offshoot 12, a first cap 14 and a second cap 16. In another embodiment of the present invention, as shown in FIG. 2, the connector 2a may comprise a housing 4a, a first valve element 6, and a second valve element 8a. The housing 4a may comprise a base portion 10a, an offshoot 12, a first cap 14 and a second cap 16a. The base portion 10, offshoot 12, first cap 14 and second cap 16 of FIG. 1 may be made of, for example, metal, plastic (e.g., polycarbonate, acrylonitrile butadiene styrene (ABS)), a composite material (i.e., two or more materials) (e.g., copolyester), or rubber. The same materials may be used for the base portion 10a, offshoot 12, first cap 14 and second cap 16a of FIG. 2. Moreover, the base portion 10, base portion 10a, offshoot 12, first cap 14, second cap 16 and/or second cap 16a may be made of the same or different materials and may be transparent or opaque. Various factors may be considered when determining the material to be used for the base portion 10, base portion 10a, offshoot 12, first cap 14, second cap 16 and/or second cap 16a, including compatibility with fluids flowing through the connector 2, 2a (i.e., material does not chemically and/or physically react with fluids flowing through the connector 2, 2a) (e.g., lipid resistance), the ability to withstand sterilization/cleaning (i.e., cleaning products used in sterilization), weight, durability, mechanical strength, resistance to bacterial formation, ease and cost of manufacturing, and ability to be attached to other materials. And, while the base portion 10, base portion 10a, offshoot 12, first cap 14, second cap 16 and/or second cap 16a are shown as cylindrical in FIGS. 1 and 2, the base portion 10, base portion 10a, offshoot 12, first cap 14, second cap 16 and/or second cap 16a may be any shape (e.g., polygonal). Various factor may be considered when determining the shape of the base portion 10, base portion 10a, offshoot 12, first cap 14, second cap 16 and/or second cap 16a, including the compatibility with standard fluid transfer devices (e.g., an intravenous tube, syringe, catheter or other connector), the desired path of fluid flow, ability of the connector 2, 2a to be flushed, and clearance around internal components (e.g., the valve elements 6 and 8, 8a).

Additionally, the base portion 10, base portion 10a, offshoot 12, first cap 14, second cap 16 and/or second cap 16a may be made, for example, by injection molding, extrusion, casting, compression molding or transfer molding and can be constructed as a single piece or may be separate pieces attached together by, for example, bonding medium (e.g., adhesive), threads, ultrasonic welding, ultraviolet curing, tape, corresponding clip and clip engaging portion(s) (e.g., a snap connection), spin welding or otherwise melting together. For example, in an embodiment of FIG. 1, the base portion 10 and offshoot 12 may have external threads (not shown) on external portions 18 and 20, respectively, to engage internal threads (not shown) of the second cap 16 and the first cap 14, respectively. Similarly, in one embodiment of FIG. 2, the base portion 10a and offshoot 12 may have external threads (not shown) on external portions 18a and 20, respectively, to engage internal threads (not shown) of the second cap 16a and the first cap 14, respectively. In another embodiment of FIGS. 1 and 2, the base portion 10, 10a and offshoot 12 may be separate pieces attached together either permanently or removeably by any of the attachment means described above. Moreover, a washer (not shown) (e.g., an O-ring) may be positioned between the base portion 10 and the second cap 16, the base portion 10a and the second cap 16a, the offshoot 12 and the first cap 14, and/or the base portion 10, 10a and the offshoot 12 to prevent fluid from leaking out of connector 2, 2a.

Alternatively, the connector 2, 2a may be molded or otherwise formed, for example, in two halves, which may be joined together by any of the means described above. In one embodiment, the base portion 10, base portion 10a, offshoot 12, first cap 14, second cap 16 and/or second cap 16a may be joined using one or more hinges (not shown). In general, a separate piece construction may allow for replacement of parts within the connector 2, 2a (e.g., the first valve element 6 and/or the second valve elements 8, 8a) and/or cleaning the inside of connector 2, 2a.

As shown in FIGS. 1 and 2, the connector 2, 2a may comprise a first port 22. All discussion herein regarding the first port 22 applies to the embodiments shown in both FIGS. 1 and 2. And, even though the construction of the first port 22 of FIGS. 3A, 3B, 4A, 4B, 5A, 5B, 6A, 6B, 8 and 9 are shown in the context of the connector 2 of FIG. 1, it should be understood that these constructions also may be incorporated in the construction of the connector 2a of FIG. 2.

The first port 22 may comprise the offshoot 12 and the first cap 14. The first port 22 may have a first channel portion 24, a main channel portion 26 containing the first valve element 6, and a connecting channel 28. The first valve element 6, however, may be located anywhere in the first port 22. The first port 22 may be constructed to receive a fluid transfer device (e.g., an intravenous tube, syringe, catheter or other connector). The fluid transfer device may be connected to the inside or outside of the first port 22. For example, the first cap 14 of the first port 22 may have external or internal threads to engage corresponding threads of a fluid transfer device. In another embodiment, the first port 22 may be connected to a fluid transfer device using a clip (not shown) on the connector 2, 2a that engages a clip receiving portion (not shown) on the fluid transfer device (i.e., a snap connection) or vice versa. In yet another embodiment, a fluid transfer device may be connected to the cap 14 by, for example, a bonding medium (e.g., adhesive), ultrasonic welding, ultraviolet curing, tape, spin welding or otherwise melting together. However, the present invention envisions all temporary and permanent means of attaching a fluid transfer device to the first port 22.

The first channel portion 24 may be any shape (e.g., cylindrical or polygonal), may taper from a proximal portion 28 to a distal portion 30 and/or may have sections with varying diameters. Various factors may be considered when determining the shape of the first channel portion 24, including the compatibility with a standard fluid transfer device (e.g., an intravenous tube, syringe, catheter or other connector), the desired path of fluid flow, and ability of the connector 2, 2a to be flushed. For example, as shown in FIGS. 1 and 2 the first channel portion 24 may have reduced diameter portions 32 and/or 33. One reason for providing reduced diameter potions 32 and/or 33 may be to form ledges 34 and/or 35, respectively, against which a fluid transfer device may abut. Such a construction may limit the distance that a fluid transfer device may be inserted into the first port 22. And, as will become apparent from the discussion below, another reason for reduced diameter portions 32 and/or 33 may be to provide a means by which valve element 22 may control fluid flow.

The first channel portion 24 may also have one or more bonding medium reservoirs 36 which may take the form of one or more recesses or grooves in the first channel portion 24 and, in particular, in the reduced diameter portion 32. The bonding medium reservoirs 36 may also be located on the outside of the first port 22 in those embodiments where a fluid transfer device is connected to the outside of the first port 22. The bonding medium reservoirs 36 may receive excess bonding medium (e.g., adhesive) when a fluid transfer device is positioned in the first channel portion 24 or on the outside of the first port 22 using a bonding medium. It should be understood that a bonding medium reservoir may receive any liquid material which may harden, including any solid material (e.g., solid plastic) that has been melted (e.g., as may result if a fluid transfer device is ultrasonically welded to the first port 22). Another function of the bonding medium reservoirs 36 may also be to prevent bonding medium and/or melted material from spreading into other portions of the first port 22 such as the main channel portion 26 and/or the connecting channel 28. Such a construction may be advantageous because bonding medium and/or melted material may affect the movement of the first valve element 6 and/or the overall flow of fluid through the first port 22.

The first valve element 6 may be positioned in the first port 22 and, in particular, in the main channel portion 26. The first valve element 6 may be made of plastic, a foam material, a composite material (i.e., two or more materials), a combination material (i.e., one material contained within another material) (e.g., a gel such as a hydrogel contained within rubber) or rubber (e.g., silicon polyisoprene) and may be formed, for example, by injection molding, extruded, casting, compression molding or transfer molding. Various factors may be considered when determining the material to be used to make the first valve element 6, including compatibility with fluid flowing through the connector 2, 2a (i.e., material does not chemically and/or physically react with fluids flowing through the connector 2, 2a) (e.g., lipid resistance), the ability to withstand sterilization/cleaning (i.e., cleaning products used in sterilization in a hospital), weight, durability, mechanical strength, resistance to bacterial formation, ease and cost of manufacturing, ability to withstand staining (i.e., from blood or other chemical products used in a hospital), ability to f10 at in fluids, and mechanical properties (e.g., resiliency; ability to be compressed, bent, folded, or otherwise contorted). And, while the first valve element 6 may be made of a material that is impermeable to fluid (i.e., does not allow fluid to pass into or through the first valve element 6 in any substantial way), the first valve element 6 may also be made of a material that is fluid permeable (i.e., allows fluid to pass into or through the first valve element 6). Moreover, the first valve element 6 may be transparent or opaque, flexible or rigid, and/or hard or soft.

Figure 2A:
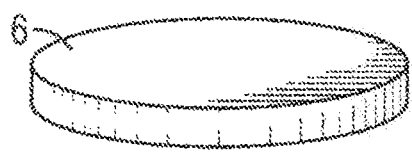
FIG. 2A is a perspective view of an exemplary embodiment of a valve element of FIGS. 1 and 2.

As shown in FIG. 2A, the first valve element 6 may be a disc which may have a thickness between about 0.004 inches and about 0.250 inches, preferably between about 0.030 inches and about 0.20 inches, and, most preferably, between about 0.03 inches and about 0.05 inches. The first valve element 6 may have a diameter between about 0.02 inches and about 0.50 inches, preferably between about 0.05 inches and about 0.25 inches, and, most preferably, between about 0.12 inches and about 0.14 inches. Various factors may be relevant in determining the thickness and/or diameter of the first valve element 6, including rigidity, flexibility, permeability, compressibility and resiliency (i.e., ability to return to original orientation after compression).

The first valve element 6 may be any shape (e.g., cylindrical, spherical, square, rectangular, triangular, conical, or polygonal), may have flat surface(s), and/or may have concave/convex surface(s). In addition, the first valve element 6 may have protrusions (e.g., protrusions 56 in FIG. 6C), indentations or ridges on a portion thereof or over its entire surface. The advantage of such a construction is described below with reference to FIGS. 6A and 6B.

Figure 4A:
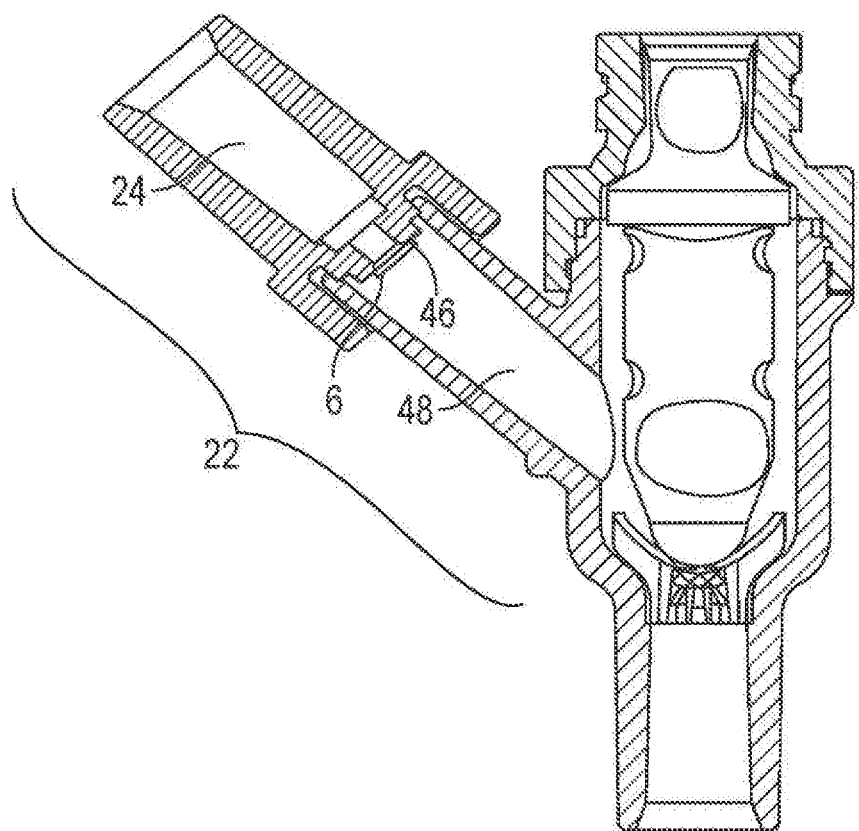
FIGS. 4A and 4B are partial cross-sectional views of another alternative exemplary embodiment of the connector of FIG. 1 with another alternative first port construction.
Figure 4B:
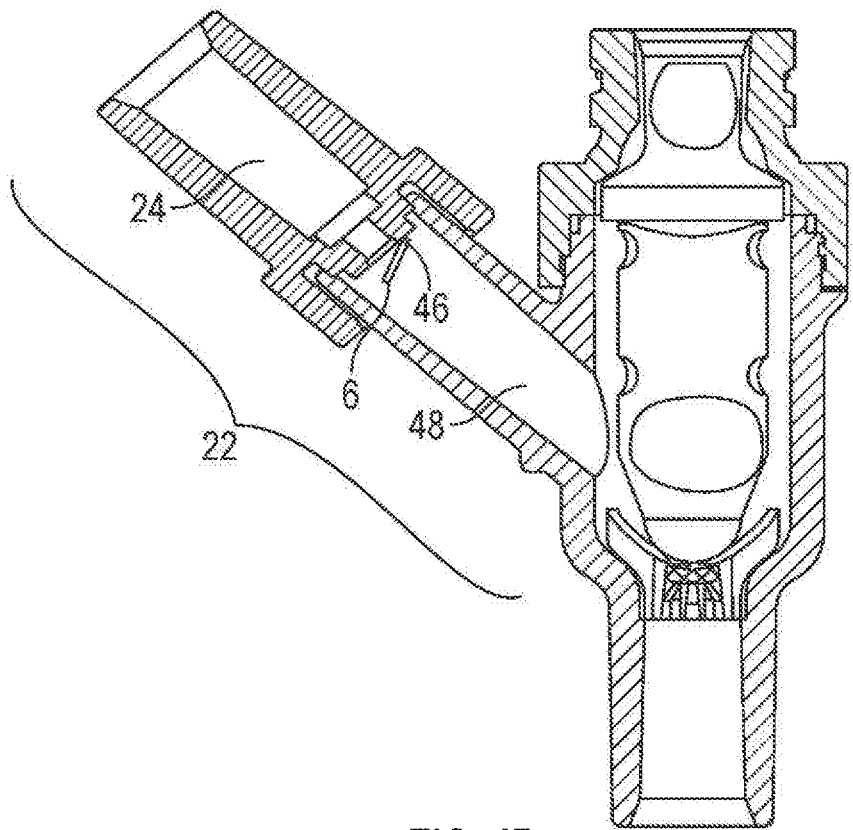

Moreover, as shown in FIGS. 1 and 2, the first valve element 6 may be freely moveable within the first port 22 (i.e., not fixedly attached to any other structure) or, as shown in FIGS. 4A and 4B, may be fixedly attached within the first port 22 such as, for example, by a hinge 46. The first valve element 6 may be positioned in the first port 22 in any way so long as fluid may flow past the valve element 6. It should be noted that the term "flow past" or any similar term using the word "past" or "pass" may mean fluid flows through or around any structure in the connector 2, 2a including any portion or the entirety of the first valve element 6 and/or the second valve element 8, 8a.

In FIGS. 1 and 2, the valve element 6 may move towards the reduced diameter portion 33 and may engage an upper stopping portion 38. In this position, fluid may be prevented from flowing past the valve element 6 (i.e., fluid may not be able to flow between the first channel portion 24 and the connecting channel 28). The first valve element 6 may also move away from the reduced diameter portion 33 and may engage a lower stopping portion 40. In this position, fluid may be able to flow past the valve element 6, for example, as will be described in detail below with reference to the fluid channels 58.

As shown in FIGS. 1 and 2, the main channel portion 26 may be larger than the first valve element 6 so that the first valve element 6 may move freely within the main channel portion 26. In an alternative embodiment, the main channel portion 26 may be substantially the same size and shape as the first valve element 6. In yet another embodiment, the main channel portion 26 may have fluid paths (not shown) through which fluid may flow past the first valve element 6. These fluid paths may extend around a portion or the entire periphery of the first valve element 6. In addition, the fluid paths may be one or more individual and separated fluid paths or may be one continuous flow path around the entire periphery of the first valve element 6.

Figure 3A:
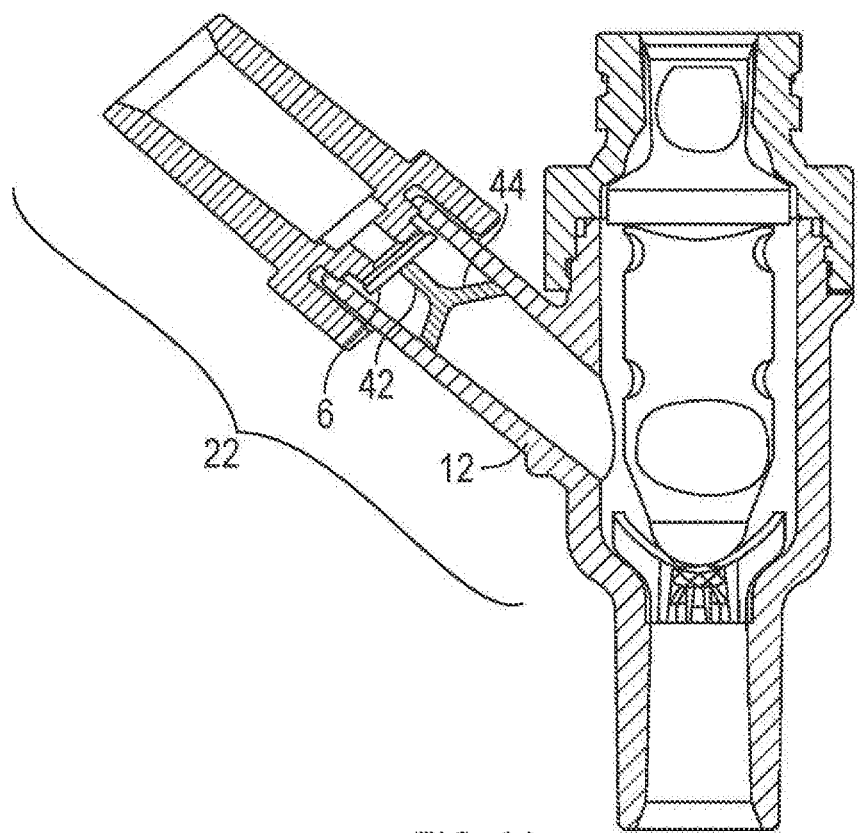
FIGS. 3A and 3B are partial cross-sectional views of an alternative exemplary embodiment of the connector of FIG. 1 with an alternative first port construction.
Figure 3B:
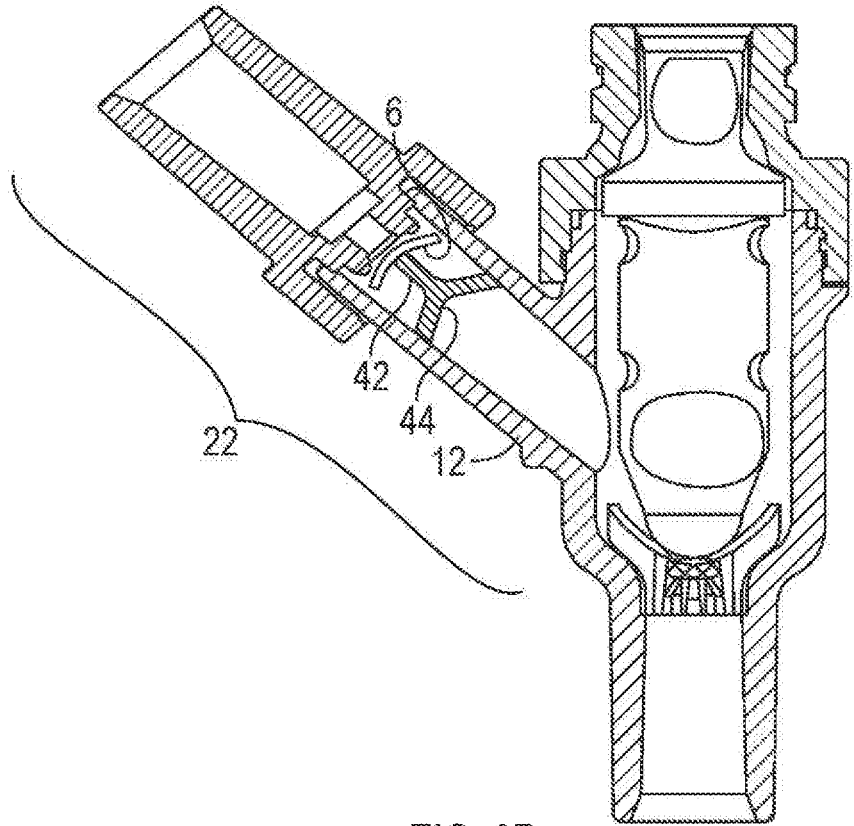

FIGS. 3A and 3B illustrate another embodiment of the construction of the first port 22. The first valve element 6 may be flexible and abutting one or more support elements 42 (e.g., prongs) positioned within the first port 22. For example, the support elements 42 may be attached to the offshoot 12 by a connecting portion 44. In one embodiment, the connecting portion 44 may be conical in shape and may have openings (not shown) which allow fluid to flow past connecting portion 44. The connecting portion 44, however, can be any structure, having any shape, that holds one or more support elements 42 within the first port 22. In use, the valve element 6 may move between an unflexed position (FIG. 3A), where fluid may be prevented from flowing past the first valve element 6, and a flexed position (FIG. 3B), where fluid may flow past the first valve element 6.

FIGS. 4A and 4B illustrate yet another embodiment of the construction of the first port 22. The first valve element 6 may be attached within the first port 22 using a hinge 46. In this embodiment, the first port 22 may comprise a first channel portion 24 and a channel 48. The channel 48 may be any size or shape so long as the first valve element 6 may move therein and allows fluid to flow past the first valve element 6. The first valve element 6 may move between a closed position (FIG. 4A), where fluid may be prevented from flowing past the first valve element 6 and an opening position (FIG. 4B), where fluid may flow past the first valve element 6.

Figure 5A:
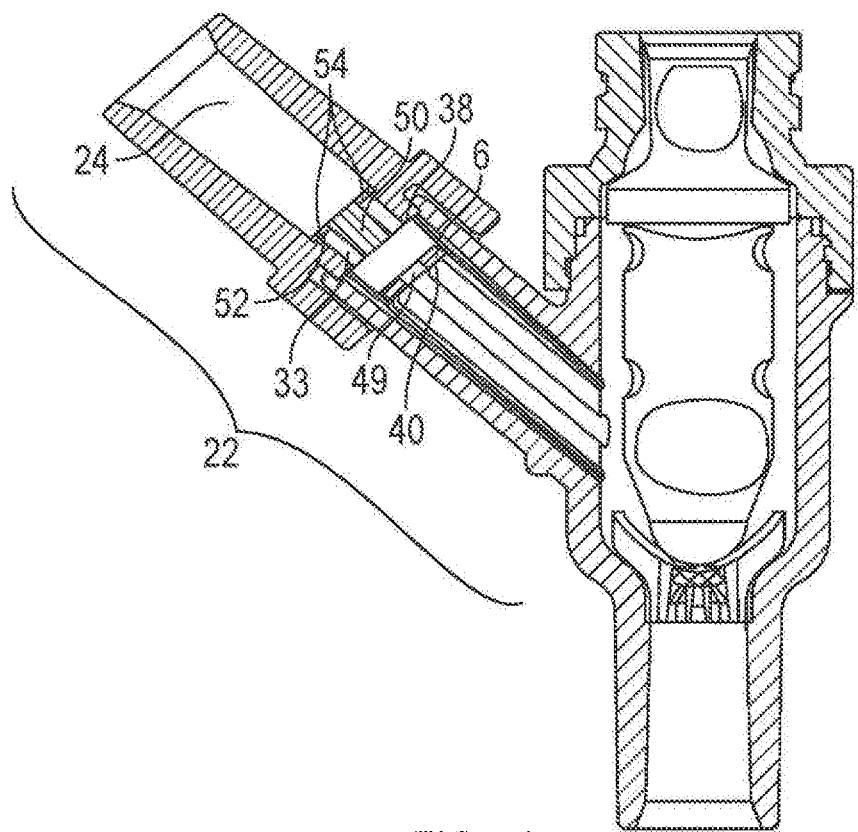
FIGS. 5A and 5B are partial cross-sectional views of another alternative exemplary embodiment of the connector of FIG. 1 with another alternative first port construction.
Figure 5B:
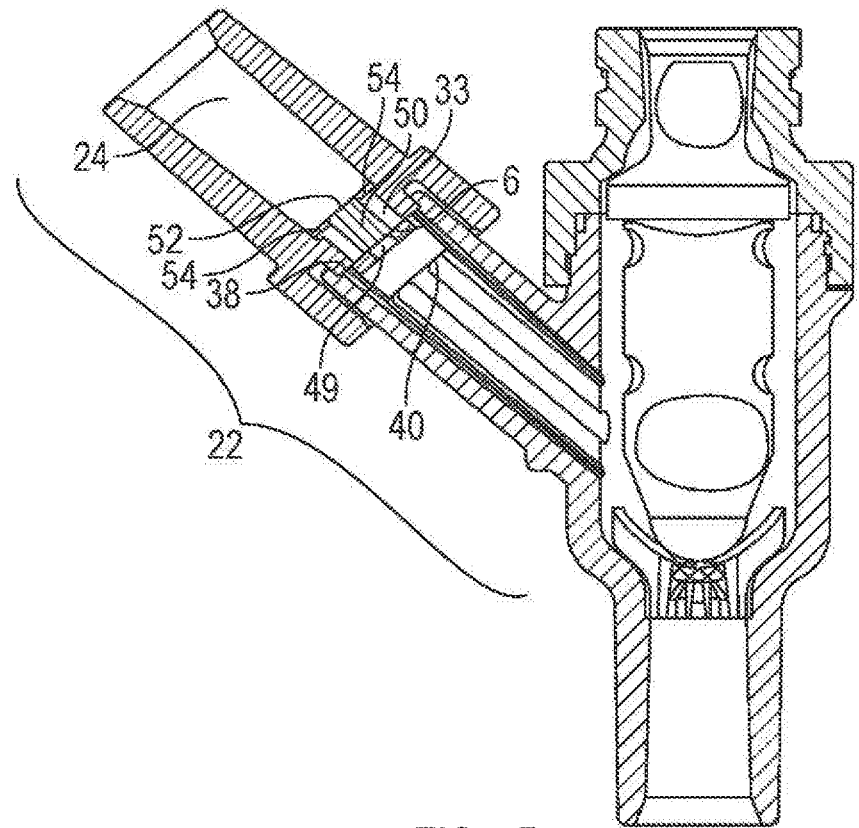
Figure 5C:
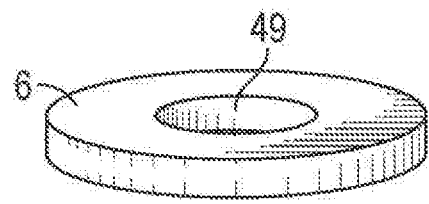
FIG. 5C is a perspective view of an exemplary embodiment of a valve element of FIGS. 5A and 5B.

FIGS. 5A and 5B show another alternative embodiment of the construction of the first port 22. As illustrated in FIG. 5C, the first valve element 6 may have a hole or opening 49. The hole 49 may be any shape or size so long as fluid may flow through the first valve element 6. The first channel portion 24 may have a portion 50, which may be held within the first channel portion 24 by a connector 52. The connector 52 may be any shape (e.g., a disc shape) and may have one or more opening 54 to allow fluid to pass therethrough. It should be understood that the connector 52 may be any structure which can hold a portion 50 within the first port 22 and allow fluid to flow past a first valve element 6.

Moreover, the portion 50 may be any shape (e.g., circular, rectangular, square, triangular, conical, cylindrical, polygon) and may have a diameter greater than the diameter of the hole 49. It should be noted that the portion 50 may be any structure that engages with the first valve element 6 and can be used to control the flow of fluid past the valve element 6. In use, as shown in FIG. 5A, the first valve element 6 may move away from the reduced diameter portion 33 and may engage the lower stopping portion 40. In this position, fluid may flow past the first valve element 6. And, as shown in FIG. 5B, the first valve element 6 may move towards the reduced diameter portion 33 and may engage the upper stopping portion 38 and portion 50. In this position, fluid may be prevented from flowing past the first valve element 6.

Figure 6A:
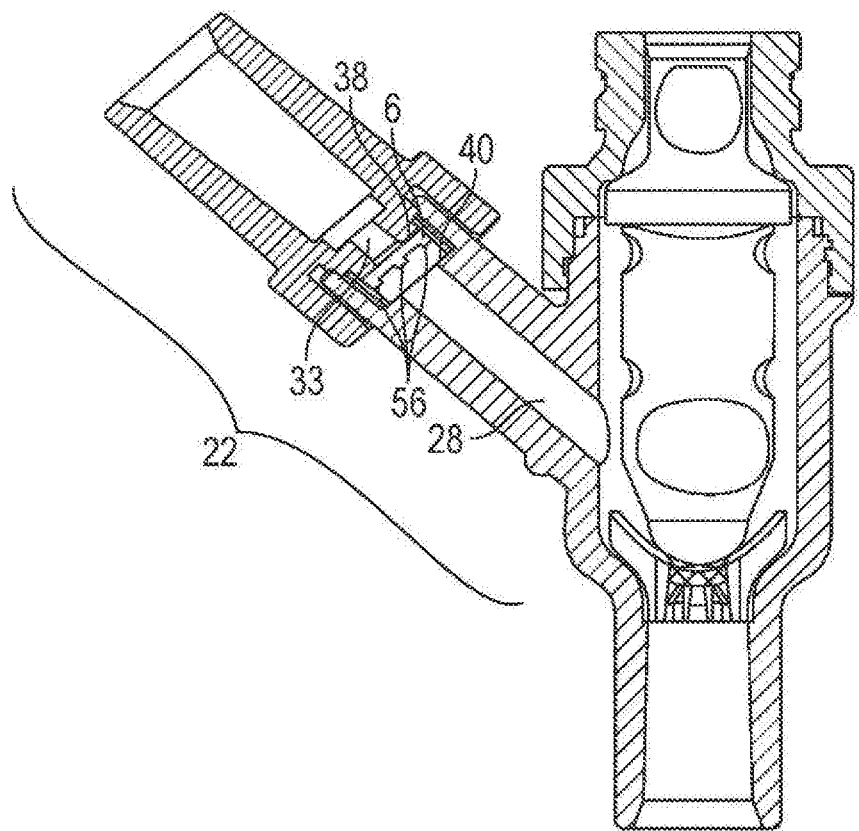
FIGS. 6A and 6B are partial cross-sectional views of another alternative exemplary embodiment of the connector of FIG. 1 with another alternative first port construction.
Figure 6B:
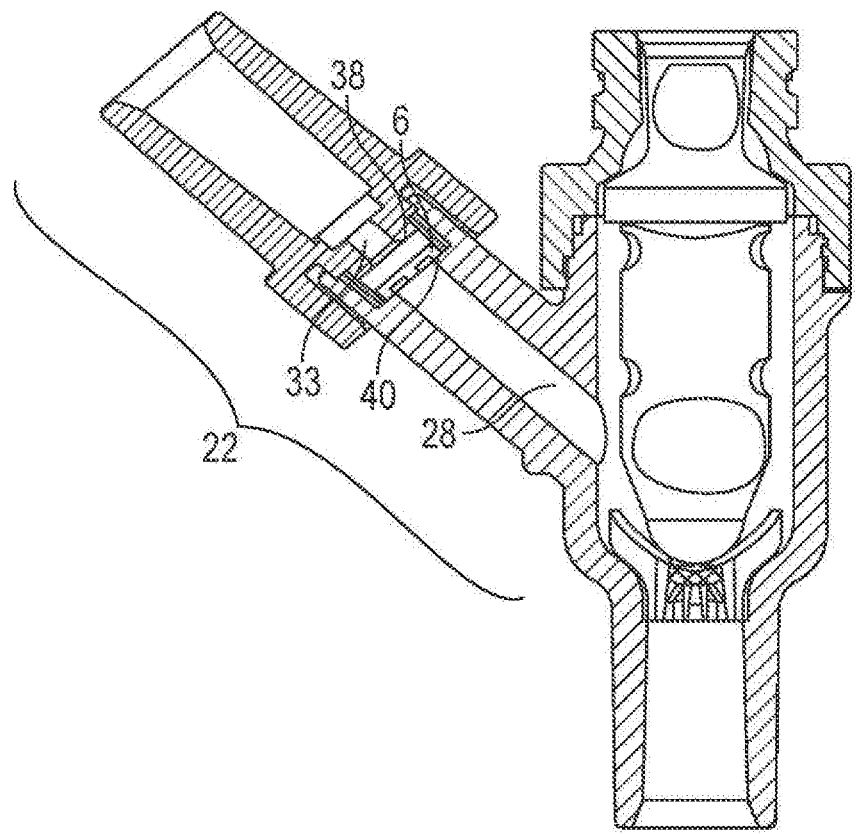
Figure 6C:
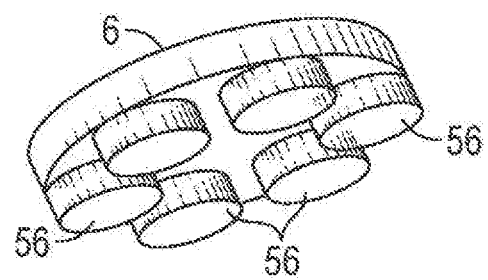
FIG. 6C is a perspective view of an exemplary embodiment of a valve element of FIGS. 6A and 6B.

FIGS. 6A and 6B illustrate another exemplary embodiment of the construction of the first port 22 where the first valve element 6 may have one or more protrusions 56 (FIG. 6C). The protrusions 56 may be formed integrally with or may be attached to the first valve element 6. As shown in FIG. 6A, the first valve element 6 may move towards the reduced diameter portion 33 and abut the upper stopping portion 38. In this position, fluid may be prevented from flowing past the first valve element 6. As shown in FIG. 6B, the first valve element 6 may move away from the reduced diameter portion 33 and abut the lower stopping portion 40. In this position, fluid may flow past the first valve element 6. The stopping portion 40 may be a solid ledge and fluid may flow past the first valve element 6 by flowing in between protrusions 56 and into the connecting channel 28 (shown in FIGS. 6A and 6B). Alternatively, the stopping portion 40 may be made up of portions of a wall 59 between one or more fluid channels 58 (FIG. 7).

Figure 7:
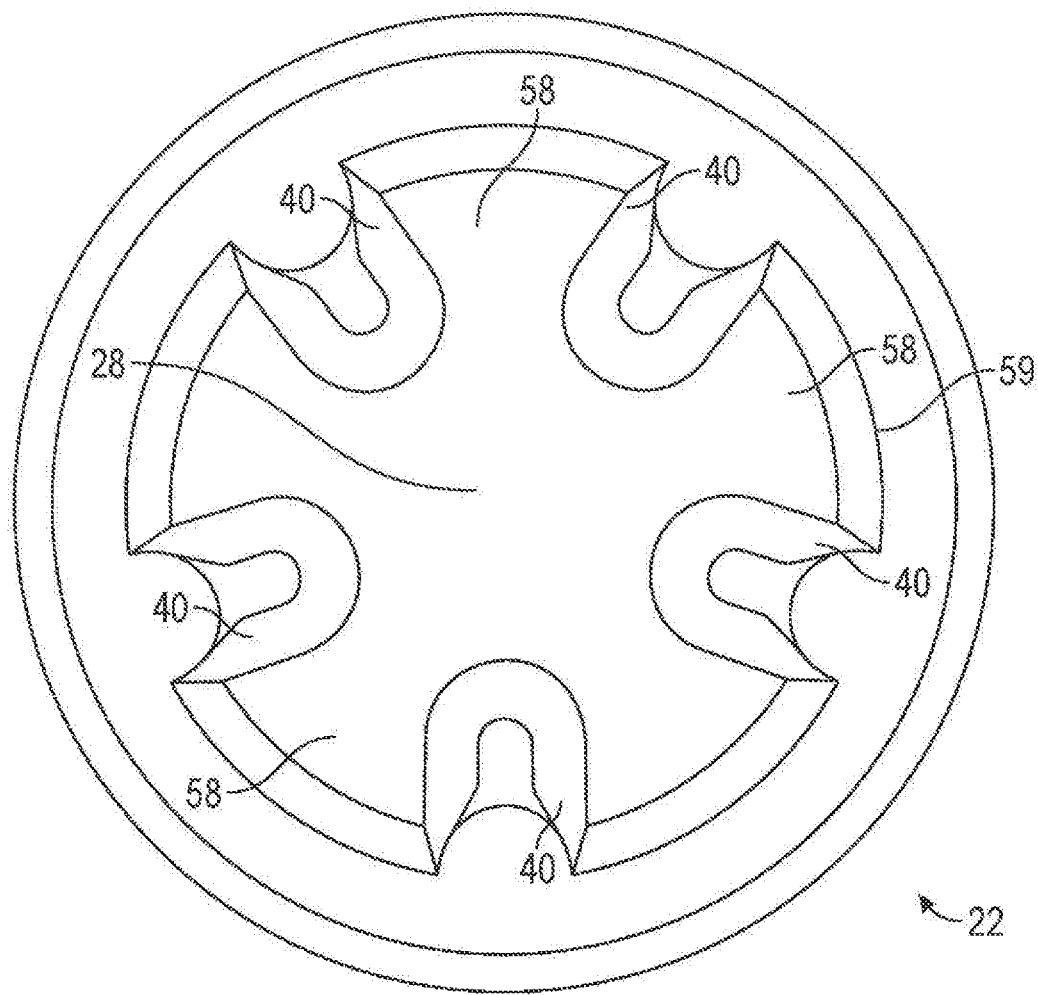
FIG. 7 is a partial cross sectional view of an exemplary embodiment of a first port of FIGS. 1 and 2 along A-A.
Figure 8:
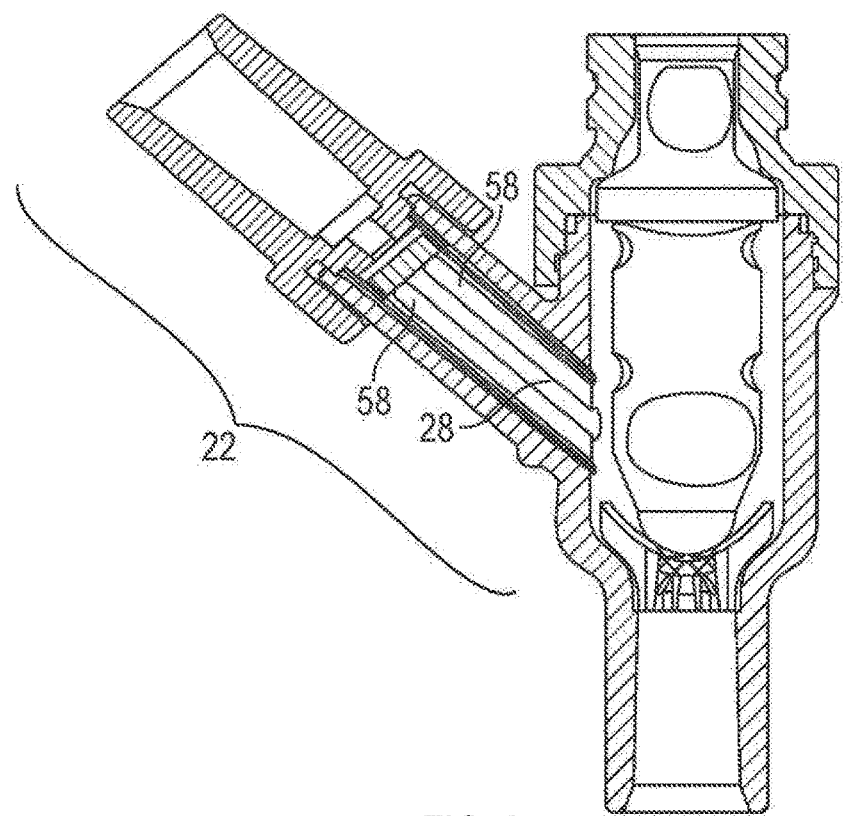
FIG. 8 is a partial cross-sectional view of an alternative exemplary embodiment of the connector of FIG. 1 with another alternative first port construction.

In any embodiment of the present invention, the first port 22 and, in particular, the connecting channel 28 may have one or more fluid channels 58 (as shown in FIG. 7 which is a view from A-A of FIGS. 1 and 2). The fluid flow channels 58 may allow fluid to flow past the first valve element 6 (e.g., around the first element 6). As shown in FIG. 7, the fluid channels 58 may be formed in the wall 59 of the first port 22. The fluid channels 58 may extend along a portion of the length of the first port 22 (shown in FIG. 1) or over a substantial length of the first port 22 (e.g., over substantially the entire length of the connecting channel 28 (shown in FIGS. 2 and 8)). As illustrated in FIG. 7, such a construction may form the lower stopping portion 40, which may abut with the first valve element 6. It should be noted, however, than any portion that abuts the first valve element 6 may be a lower stopping portion 40.

The shorter fluid channels 58 (such as those of FIG. 1) may be effective in controlling fluid flow past the first valve element 6 and into a connecting channel 28. This design may prevent the formation of air bubbles within the first port 22 (in particular, below the first valve element 6); air bubbles may present health risks to a patient (especially children and the elderly). In contrast, longer fluid channels 58 (such as those in FIG. 2) may not control the flow of fluid around the first valve element 6 as well as shorter fluid channels 58 and may result in air bubbles. Moreover, short fluid channels 58 may provide the additional advantages of reducing the priming and/or flush volumes, which may result in increased efficiency of fluid delivery to a patient. Other reasons for varying the length of the fluid channels 58 will also be appreciated by those skilled in the art. It should, however, be understood that the fluid channels 58 can extend any distance within the first port 22.

Further, the fluid channels 58 may be formed as part of the first port 22 or as part of a separate piece (not shown), which may be inserted into the first port 22. As part of the first port 22, the fluid channels 58 may be made of the same material as the first port 22. The separate piece may be made, for example, of metal, plastic (e.g., polycarbonate, acrylonitrile butadiene styrene (ABS)), a composite material (i.e., two or more materials) (e.g., copolyester) or rubber. The separate piece may be made of the same material as or a different material from the first port 22. Various factors may be considered when determining the material used for the separate piece, including compatibility with fluids flowing through the connector 2, 2a (i.e., the material does not react with fluids flowing through the connector 2, 2a) (e.g., lipid resistance), the ability to withstand sterilization/cleaning (i.e., cleaning products used in sterilization), weight, durability, mechanical strength, resistance to bacterial formation, ease and cost of manufacturing, and ability to be attached to other materials. The separate piece may be attached to the inner wall of first port 22, for example, by a bonding medium (e.g., adhesive), threads, ultrasonic welding, ultraviolet curing, corresponding clip and clip engaging portion (s) (e.g., a snap connection), spin welding or otherwise melting together. In an embodiment where an operator can gain access to the inside of the connector 2, the separate piece may be replaceable.

Figure 9:
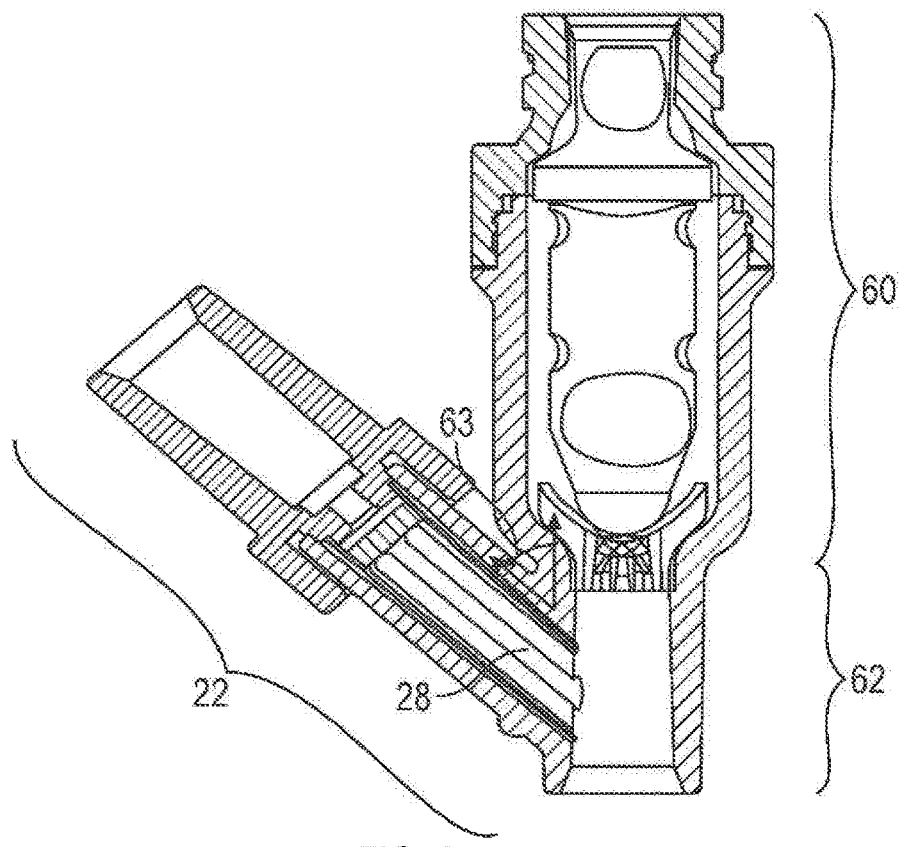
FIG. 9 is a partial cross-sectional view of an alternative exemplary embodiment of the connector of FIG. 8 with the first port located in an alternative position.

Turning now to the interconnection between ports, the first port 22 may be connected to a second port 60, 60a as shown in FIGS. 1 and 2, respectively. The second port 60, 60a may be integral with the first port 22 or may be attachable to the first port 22. Alternatively, as shown in the embodiment of FIG. 9, the first port 22 may be connected to the third port 62. Moreover, in one embodiment of FIG. 2, while not shown, the first port 22 may be connected to the third port 62a.

In an embodiment where the first port 22, second port 60, 60a and/or third port 62, 62a are all separate pieces, one port may be permanently or removeably connected to another port, for example, by a bonding medium (e.g., adhesive), threads, ultrasonic welding, ultraviolet curing, tape, corresponding clip and clip engaging portion(s) (e.g., a snap connection), spin welding or otherwise melting together. Where the ports are removeably connected to each other, an operator may gain entry to the interior of the connector 2, 2a and may be able to replace components therein and/or clean the inside of the connector 2, 2a.

Furthermore, the first port 22 may intersect the second port 60, 60a and/or third port 62, 62a (e.g., FIG. 9) at an angle 63, 63a of between about 15 degrees and about 165 degrees, more preferably between about 30 degrees and about 60 degrees and, most preferably, between about 40 degrees and about 50 degrees. The second port 60, 60a may intersect the third port 62, 62a at an angle 63' between about 15 degrees and about 180 degrees, more preferably between about 90 degrees and about 180 degrees and, most preferably, 180 degrees. The angle chosen may be a consideration of various factors, including ease of injection/withdrawal of fluid, weight of the connector 2, 2a in a natural hanging position, and prevention of tube kinking. Moreover, the third port 62, 62a may intersect the side 61, 61a of the second port 60, 60a at any angle describe above.

As shown in FIGS. 1 and 2, a second port 60, 60a may comprise the base portion 10, 10a and second cap 16, 16a. A fluid transfer device (not shown) (e.g., an intravenous tube, syringe, catheter, or other connector) may engage the second port 60, 60a. For example, the second cap 16, 16a may have an external threaded portion 23, 23a (or an internal threaded portion (not shown)) to engage a corresponding threaded portion of a fluid transfer device. All means for attaching a fluid transfer device to the second port 60, 60a, however, are envisioned (e.g., clip and a corresponding clip engaging portion(s), tape, etc.). Such a design may allow for the fluid transfer device to be held securely onto the second port 60, 60a when fluid is transferred between a fluid transfer device and the second port 60, 60a.

Further, the base portion 10, 10a and second cap 16, 16a may define a channel 64, 64a. The channel 64, 64a may, in turn, comprise a proximal channel 66, 66a located at a proximal end 68, 68a and a main channel 70, 70a. The inner surface of the channel 64, 64a may be smooth or may have, for example, grooves, slots, protrusions, ridges or ribs. For example, one or more fluid passageways 69, 69a may be provided in the second cap 16, 16a. The fluid passageways 69, 69a may be one or more individual longitudinal channels or, as shown in FIGS. 1 and 2, a widened diameter portion around the entire inner surface of proximal channel 66, 66a. Moreover, as illustrated in FIG. 2, the main channel 70a may have ribs 71a, which may have fluid paths therebetween. Such internal structure(s) may be provided, for example, to guide the flow of fluid past the second valve element 8, 8a.

Furthermore, the second valve element 8, 8a may be positioned within second port 60, 60a. It should, however, be noted that one skilled in the art would appreciate that the second valve element 8, 8a may be any needless access device such as, for example, those disclosed in U.S. Pat. Nos. 5,676,346; 5,360,413; 5,300,034; 5,242,432; and 5,230,706. In the embodiments shown in FIGS. 1 and 2, the second valve element 8, 8a may comprise a head portion 72, 72a and a body portion 74, 74a. The head portion 72, 72a and the body portion 74, 74a may be one integral piece or separate pieces. And, as shown in FIGS. 1 and 2, the head portion 72, 72a and/or body portion 74 may be made of a solid piece of material and the body portion 74*a* may be hollow. However, the head portion 72, 72*a* or the body portion 74 may also be hollow and the body portion 74*a* may also be a solid piece of material.

As shown in FIG. 2, the body portion 74*a* may have a wall 75*a* defining an internal chamber 77*a*, which may contain fluid (e.g., air). The wall 75*a* may be solid (i.e., there are no holes or openings therethrough). As will be discuss in further detail below with regard to the use of the connector 2*a*, this construction may provide significant advantages when the air contained inside the internal chamber 77*a* may flow in and out of the connector 2*a* through one or more channels 11*a*, which may communicate with the outside of the connector 2*a*. In another embodiment where the head portion 72, 72*a* and/or body portion 74, 74*a* may be hollow, there may be one or more openings (not shown) in the head portion 72, 72*a* and/or body portion 74, 74*a*. Fluid may be able to flow through the opening(s) and into and through the head portion 72, 72*a* and/or body portion 74, 74*a*.

Further, the head portion 72, 72*a* and body portion 74, 74*a* may be made of the same or different materials such as, for example, plastic, a foam material, a composite material (i.e., made of two or more materials), a combination material (i.e., one material contained within another material) (e.g., a gel such as a hydrogel contained within rubber) or rubber (e.g., silicon polyisoprene) and may be transparent or opaque. The material may be elastomeric (i.e., compressible, stretchable, bendable, flexible, foldable or otherwise contortable). Various factors may be considered when determining the material to be used for the head portion 72, 72*a* and body portion 74, 74*a*, including compatibility with fluids flowing through the connector 2, 2*a* (i.e., the material does not react with fluids flowing through the connector 2, 2*a*) (e.g., lipid resistance), the ability to withstand sterilization/cleaning (i.e., cleaning products used in sterilization), weight, durability, resistance to bacterial formation, ease and cost of manufacturing, ability to be attached to other materials, and mechanical properties (e.g., strength, resiliency; ability to be compressed, twisted, bended, folded, or otherwise contorted). Moreover, the head portion 72, 72*a* and body portion 74, 74*a* may be formed, for example, by injection molding (e.g., liquid injection molding), casting, or extrusion and may be any shape (e.g., polygonal or spherical head; polygonal or cylindrical body).

In embodiments where the head portion 72, 72*a* and body portion 74, 74*a* may be made of separate pieces, the head portion 72, 72*a* and body portion 74, 74*a* may be connected, for example, by a bonding medium (e.g., adhesive), threads, ultrasonic welding, ultraviolet curing, spin welding or otherwise melting together.

The second valve element 8, 8*a* may also comprise one or more grooves, recesses, notches (e.g., notches 76, 76*a*) which may be located in the head portion 72, 72*a* and/or the body portion 74, 74*a* or both. As shown in FIG. 2, the body portion 74*a* may also comprise one or more undercuts 79*a*. Further, notches 76, 76*a* may be located anywhere on the outer surface of the head portion 72, 72*a* and/or body portion 74, 74*a*. And where the head portion 72, 72*a* and body portion 74, 74*a* are hollow, or have a wall, notches 76, 76*a* may be located anywhere on the inner surface of the head portion 72, 72*a* and/or body portion 74, 74*a*.

The notches 76, 76*a* and/or undercuts 79*a* may facilitate compression, bending, canting, folding, and/or contorting of the second valve element 8, 8*a*. In addition, compression, bending, canting, folding, and/or contorting may also be facilitated by the head portion 72, 72*a* and/or body portion 74, 74*a* being molded in a pre-cant position (such as shown in body portion 74 of FIG. 1). Moreover, the notches 76, 76*a* and/or undercuts 79*a* may assist in guiding fluid flow through the second port 60, 60*a*, for example, when the valve element 8, 8*a* is a compressed, bent, canted, folded, and/or contorted position.

The notches 76, 76*a* and undercuts 79*a* may be any shape (e.g., round, elliptical, square, rectangular or polygonal), size, and may cover any amount of area of the head portion 72, 72*a* and/or body portion 74, 74*a*. As shown in the embodiment of FIG. 1, notches 76 may be smile cuts along a portion of the outer area of both the head and body portions 72, 74. And, as shown in FIGS. 2, notches 76*a* may be a smile cut in the head portion 72*a*.

The head portion 72, 72*a* may comprise a first enlarged portion 78, 78*a* which may seal opening portion 80, 80*a*. The head portion 72, 72*a* may also have a second enlarged portion 81, 81*a* which may engage a shoulder portion 83, 83*a* of the second cap 16, 16*a*. The enlarged portions 78, 78*a* and/or 81, 81*a* may prevent fluid from flowing past the second valve element 8, 8*a*.

Furthermore, a top 67, 67*a* of the second valve element 8, 8*a* may be substantially flush with respect to the top 73, 73*a* of the second cap 16, 16*a*. Such a construction may allow for antiseptic swabbing of the tops 67, 67*a* and 73, 73*a*. In another embodiment, not shown, the top 67, 67*a* of the second valve element 8, 8*a* may protrude out of the second cap 16, 16*a* or may be sunken into the second cap 16, 16*a*. These constructions may also allow for antiseptic swabbing. Where top 67, 67*a* of the second valve element 8, 8*a* may be sunken into cap 16, 16*a*, the top 67, 67*a* may be below the level of the top 73, 73*a* of the second cap 16, 16*a*. Additionally, the top 67, 67*a* of the second valve element 8, 8*a* may be flat or may have protrusions (not shown) extending therefrom. The protrusions may help guide fluid flow past the second valve element 8, 8*a*.

Moreover, in one exemplary embodiment (not shown), the second valve element 8 may comprise only a head portion 72 (i.e., no body portion 74). The head portion 72 may be fixed to the proximal portion 68 of the second port 60 and, in particular, may be fixed in the second cap 16. The head portion 72 may be fixed by, for example, a bonding medium (e.g., adhesive), ultrasonic welding, ultraviolet curing, spin welding or otherwise melting together. Alternatively, the head portion 72 may have one or more protruding portions (not shown) which may be engage within receiving portion(s) (not shown) in the second port 60. The head portion 72 may also have a resealable pre-slit orifice or opening (not shown) therethrough for receiving a fluid transfer device. In this way, fluid may be transferred between the fluid transfer device and the second port 60.

In another embodiment, where the second valve element 8 may only comprise a head portion 72, the head portion 72 may be a solid piece (i.e., no slits or opening therethrough) of rigid or flexible material and may have a biasing member (not shown), which may be located at a distal end 82 of the head portion 72 and may bias head portion 72 into proximal channel 66. The biasing portion may be stretchable, and may be, for example, an annular flange around the distal end 82 of the head portion 72 or one or more flange portions. It should be understood that an annular flange can be any shape (e.g., circular, square, rectangular, polygonal).

In one embodiment, the biasing member may be contained between the second cap 16 and the base portion 10 at location 84. The biasing member may have space between one or more flange portions or, where the biasing member is an annular flange, may have one or more opening therein. When a fluid transfer device is inserted into the second port 60, the head portion 72 may be pushed down into the second port 60. The biasing member and, consequently, the space and/or openings may stretch. In this embodiment, fluid may flow past the head portion 72, through the space and/or openings in the biasing member, and into main channel 70. Further, a head portion 72 made of a rigid material or containing a pin or rod therethrough (e.g., a solid piece of plastic or metal through the head portion 72) may improve the performance of this embodiment-having a rigid head portion may make it easier to stretch the biasing member upon insertion of a fluid transfer device into the second port 60.

In yet another embodiment, the second valve element 8 may be biased by a spring (not shown) positioned around the body portion 74 of the second valve element 8 and held, for example, between the enlarged portion 81 and the housing 4-including the wall of the housing 4 and any portion connected/connectable to the housing 4 (e.g., the valve support 86 (discussed below)). Alternatively, a spring may be positioned below the second valve element 8 (i.e., between the body portion 74 and the housing 4).

Referring again to FIGS. 1 and 2, the body portion 74, 74a may bias the head portion 72, 72a into the proximal channel 66, 66a. It should be understood by those skilled in the art that the body portion 74, 74a may be any structure (e.g., a spring (not shown)) which can bias the head portion 72, 72a into the proximal channel 66, 66a. Moreover, the body portion 74, 74a may be fixed or rest freely with respect to the housing 4, 4a.

For example, as shown in FIGS. 2, the second valve element 8a may have a circular flange 80a. The circular flange 80a may be captured between the base portion 10a and the second cap 16a. In particular, the circular flange 80a may be captured between the base portion 10a and one or more ribs 71a of the second cap 16a. In an alternative embodiment, the second valve element 8a may have one or more flange portions. In yet another embodiment of FIGS. 2, the valve element 8a may be connected to the base portion 10a, for example, by a bonding medium (e.g., adhesive), threads, ultrasonic welding, ultraviolet curing, spin welding or otherwise melting together. Such constructions may fix the second valve element 8a within the housing 4a.

Figure 10:
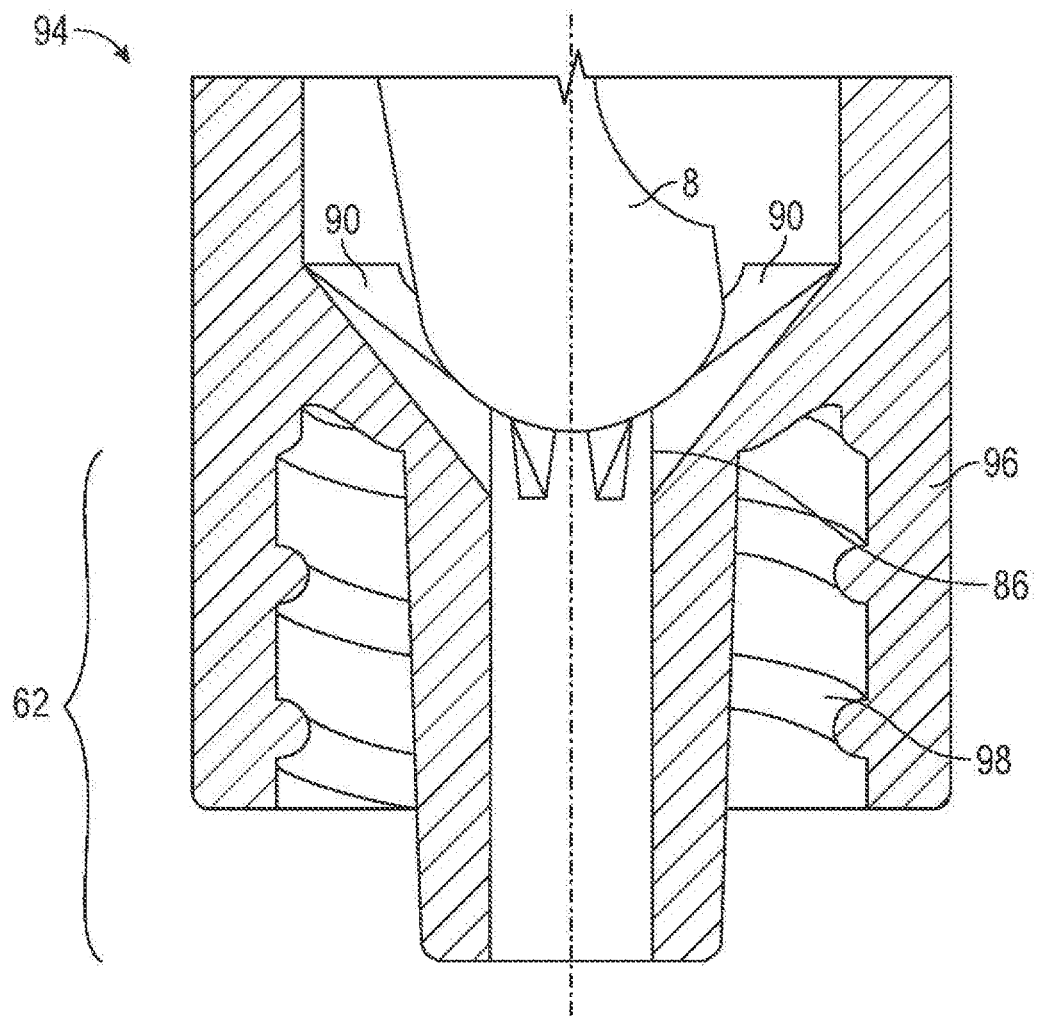
FIG. 10 is a partial cross-sectional view of an alternative exemplary embodiment of the distal portion of the connector of FIG. 1.

Alternatively, the body portion 74 may freely rest or be fixed with respect to a valve support 86. As shown in FIGS. 1, the valve support 86 may be positioned in the channel 64 of the second port 60 and/or channel 88 of the third port 62. The valve support 86 may support the second valve element 8 and may comprise one or more holding ribs 90 and a valve seat 92. However, as shown in FIGS. 10, in an alternative embodiment, the valve support 86 may comprise holding ribs 90 and no valve seat 92. The holding ribs 90 and/or the valve seat 92 may have a concave shape, but, any other shape may also be used. One or more fluid flow channels 93 may be located between holding ribs 90. The fluid flow channels 93 may enable fluid to flow past the second valve element 8. It should be noted, however, that the valve support 86 can be any structure located anywhere within the second and/or third ports 60, 62, so long as the valve support 86 supports the second valve element 8 and allows fluid to flow past the second valve element 8.

Further, the holding ribs 90 and the valve seat 92 may be made of metal, plastic (e.g., polycarbonate, acrylonitrile butadiene styrene (ABS)), a composite material (i.e., two or more materials) (e.g., copolyester), or rubber and may be transparent or opaque. The holding ribs 90 and the valve seat 92 may be made of the same or different materials from each other and/or the ports 60, 62. Various factors may be considered when determining the material to be used for the holding ribs 90 and the valve seat 92 including, compatibility with fluids flowing through the connector 2 (i.e., material does not chemically and/or physically react with fluids flowing through the connector 2) (e.g., lipid resistance), the ability to withstand sterilization/cleaning (i.e., cleaning products used in sterilization), weight, durability, mechanical strength, resistance to bacterial formation, ease and cost of manufacturing, and ability to be attached to other materials.

Additionally, the holding ribs 90 and/or the valve seat 92 may be integral with the surface of the channels 64, 88 or may be separate from each other and/or the channels 64, 88. If made of separate pieces, the holding ribs 90 and valve seat 92 may be connected to one another and/or channels 64, 88 by, for example, a bonding medium, threads, ultrasonic welding, ultraviolet curing, spin welding or otherwise melting together. And, if the housing 4 is designed to allow access therein, the holding ribs 90 and/or valve seat 92 may be replaceable. Moreover, in an embodiment where the third port 62 may be connected to the side 61 of the second port 60, the second valve element 8 may be supported on the wall of the housing 4 (as shown in FIGS. 11) and valve support 86 may be unnecessary.

Turning now to the third port 62, 62a, the third port 62, 62a may be an integral part of the second port 60, 60a or may be attachable to the second port 60, 60a. The third port 62, 62a may be any shape (e.g., cylindrical, rectangular, polygonal) and/or size. Various factors may be considered when determining the shape of the third port 62, 62a, including compatibility with a standard fluid transfer device, the desired path of fluid flow, and the ability of the connector 2, 2a to be flushed.

FIGS. 10 shows an alternative configuration of the third port 62 in the distal portion 94 of the connector 2 of FIGS. 1. In this embodiment, as well as in FIGS. 2, the third port 62, 62a may be surrounded by a wall portion 96, 96a which may contain internal threads 98, 98a for engaging corresponding threads (not shown) of a fluid transfer device.

Figure 11:
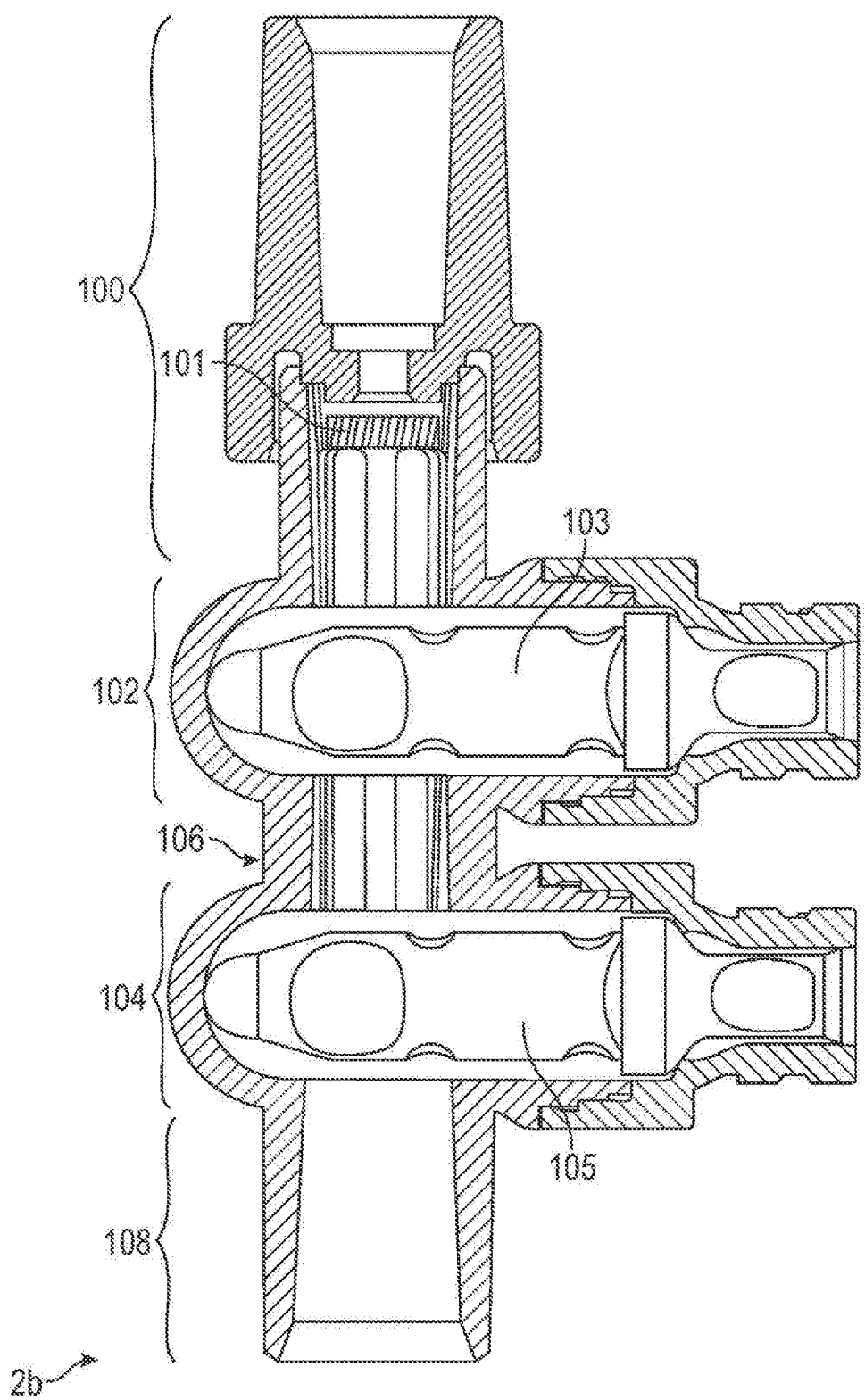
FIG. 11 is a partial cross-sectional view of an alternative exemplary embodiment of the connector of the present invention.
Figure 12:
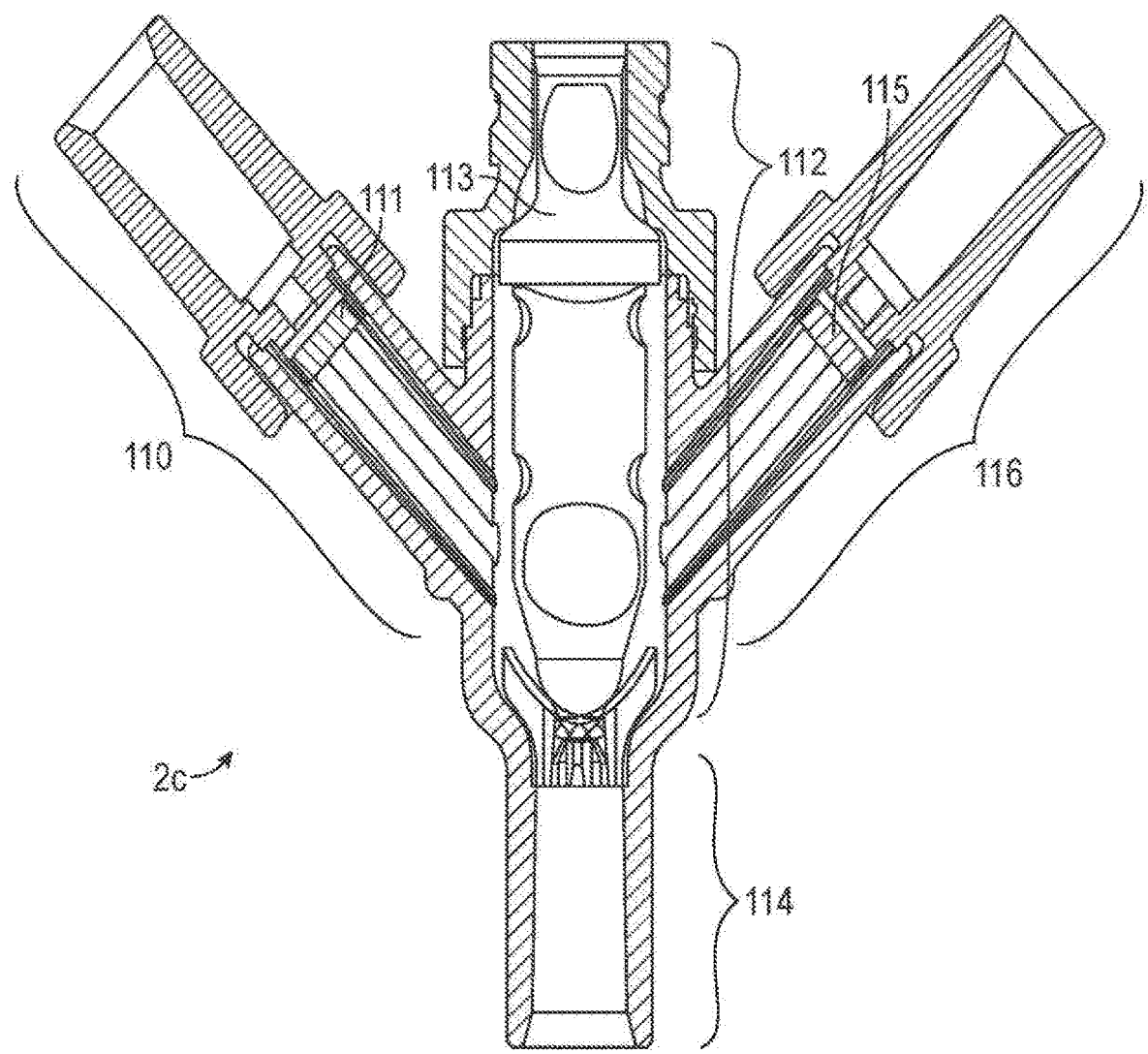
FIG. 12 is a partial cross-sectional view of an alternative exemplary embodiment of the connector of FIG. 1 with an additional port.

Furthermore, as shown in FIGS. 11 and 12, other arrangements of the first, second and third ports are also envisioned as part of the present invention. For example, the connector 2b of FIGS. 11 may comprise a first port 100 having a first valve element 101, a second port 102 having a second valve element 103, a fourth port 104 having a third valve element 105, a third port or connecting port 106 between the second port 102 and fourth port 104, and a fifth port 108. The connector 2c of FIGS. 12 may comprise first port 110 having a first valve element 111, a second port 112 having a second valve element 113, a third port 114, and a fourth port 116 having a third valve element 115. While the embodiments in FIGS. 11 and 12 may have more ports and valve elements than in FIGS. 1 and 2 and may have different port orientations, the ports and valve elements of FIGS. 11 and 12 may be arranged in the same orientation and configured with the same components and materials as described above with regards to the first port 22, the second port 60, 60a, the third port 62, 62a, first valve element 6 and the second valve element 8, 8a. Moreover, the connectors 2b (FIGS. 11) and 2c (FIGS. 12) (as well as their ports and valve elements) may function and may be used in the same way as described in detail below for FIGS. 1 and 2.

Moreover, it should be noted that any of the components of the present invention, including the specific embodiments described herein, may incorporate an antimicrobial compound or may have an antimicrobial coating covering a portion or the entire surface of the components. The antimicrobial compound or coating may inhibit the growth of bacteria. An antimicrobial material may be formed, for example, by adding a commercially available antimicrobial compound such as Agion™ produced by Agion™ Technologies Inc. of Wakefield, Mass., to, for example, plastic or rubber. This material, in turn, may be used to make a component of the present invention. Alternatively or in addition, an antimicrobial compound may be sprayed, painted or otherwise affixed to the surface of any component of the present invention and, thus, form a coating thereon.

In use, a portion of a first fluid transfer device 200, 200a (e.g., intravenous tube, syringe, catheter, or other connector) may be connected (either permanently or removeably) to the first port 22. The other end of the first fluid transfer device 200, 200a may be connected to, for example, an intravenous bag. For example, one end of an intravenous tube may be inserted into the first port 22 and the other end may be inserted into an intravenous bag. A second fluid transfer device 202, 202a, for example, another intravenous tube may connect the third port 62, 62a to a patient. The path of fluid flow from the first fluid transfer device 200, 200a, through the first port 22, the second port 60, 60a, the third port 62, 62a, and into the second fluid transfer device 202, 202a may form part of a main fluid line. As shown for example in FIGS. 1, 2, 3B, 4B, 5A and 6B, the first valve element 6 may be in a first position as a first fluid flows past the first valve element 6. The first fluid may flow through connecting channel 28, into the second port 60, 60a and through the channel 88, 88a of third port 62, 62a. In an alternative embodiment such as FIGS. 9, the first fluid may flow directly from the first port 22 (e.g., through the connecting channel 28) to the third port 62, 62a. In another embodiment of the connector 2 (FIGS. 1), as the first fluid flows between the second port 60 and the third port 62, the first fluid may flow through the valve support 86. In addition, in embodiments comprising the fluid channels 58, the first fluid may flow through the fluid channels 58.

Furthermore, an operator may use the second port 60, 60a to transfer a second fluid into the connector 2, 2a (e.g., into the main intravenous line) and/or transfer fluid from the connector 2, 2a. To accomplish this, a third fluid transfer device 204, 204a may be connected to the second port 60, 60a. A portion (e.g., a male luer) of the third fluid transfer device 204, 204a may be inserted into the second port 60, 60a. In the embodiments of FIGS. 1 and 2, insertion of the third fluid transfer device 204, 204a into the second port 60, 60a may result in compression, canting, bending, folding, and/or contorting of the second valve element 8, 8a within the second port 60, 60a (i.e., the head portion 72, 72a and/or body portion 74, 74a may compress, cant, bend, fold, and/or contort). In other words, the axis (not shown) of the second valve element 8, 8a may be displaced from the axis (not shown) of the second port 60, 60a. And, the top 67, 67a of the second valve element 8, 8a may move from a first position (shown in FIGS. 1 and 2), where the top 67, 67a may be substantially flush with the top 73, 73a, to a second position. It should be understood that a second position may be any position which is not the first position.

In an exemplary embodiment where the third fluid transfer device 204, 204a has threads (not shown) to engage the external threaded portion 23, 23a of the second port 60, 60a, as the third fluid transfer device 204, 204a is threaded onto the second port 60, 60a, the second valve element 8, 8a may continue to compress, cant, bend, fold, and/or contort (and possibly twist) and may move further down into the second port 60, 60a. And, as the third fluid transfer device 204, 204a moves farther into the second port 60, 60a, the second valve element 8, 8a may move out of proximal channel 66, 66a into a second position (e.g., within the main channel 70, 70a). In FIGS. 2, insertion of the third fluid transfer device 204a may also result in the air contained in chamber 77a moving through channels 11a and out of connector 2a.

In a second position, fluid may flow past the second valve element 8, 8a. In an embodiment comprising the first enlarged portion 78, 78a and fluid passageways 69, 69a, fluid may flow past the second valve element 8, 8a as the first enlarged portion 78, 78a moves past the fluid passageways 69, 69a. In an embodiment where there are no fluid passageways 69, 69a, fluid may flow past the second valve element 8, 8a as the first enlarged portion 78, 78a moves out of the proximal channel 66, 66a and into the main channel 70, 70a. In an embodiment without the first enlarged portion 78, 78a fluid may flow past the second valve element 8, 8a at any time after the third fluid transfer device 204, 204a is positioned adjacent to the top 67, 67a of the second valve element 8, 8a.

Moreover, the flow of fluid between the proximal channel 66, 66a and the main channel 70, 70a may be prevented when the second enlarged portion 81, 81a engages an inner portion of the second port 60, 60a (e.g., shoulder portion 83, 83a). Upon disengagement of the second enlarged portion 81, 81a from an inner portion of the second port 60, 60a (e.g., shoulder portion 83, 83a), fluid may flow between the proximal channel 66, 66a and the main channel 70, 70a.

When the second valve element 8, 8a is in a second position, the second fluid may be transferred to the second port 60, 60a from the third fluid transfer device 204, 204a and may combine with the first fluid. It should be understood that the term "combine" can mean that the first and the second fluid join to form a homogenous third fluid (e.g., dilution of a medication in saline) or that the first and second fluids may remain separate from one another (e.g., blood in water; oil in water). Alternatively, the first fluid may be transferred to the third fluid transfer device 204, 204a from the second port 60, 60a (i.e., fluid may be withdrawn from the connector 2, 2a).

As the second fluid is transferred to the second port 60, 60a from the third transfer device 204, 204a, the first valve element 6 may move from the first position to a second position as shown, for example, in FIGS. 3A, 4A, 5B, and 6A. It should be understood that a second position may be any position that is not the first position. In a second position, fluid may be prevented from flowing past the first valve element 6 in a direction towards the first fluid transfer device 200, 200a. The movement of the first valve element 6 from the first to a second position may be the result of fluid pressure created by the transfer of the second fluid from the third fluid transfer device 204, 204a to the second port 60, 60a. Alternatively, the movement of the first valve element 6 may also result from the insertion of the third fluid transfer device 204, 204a into the second port 60, 60a.

In general, with reference to FIGS. 1 and 2, when the second fluid is transferred from the third fluid transfer device 204, 204a to the second port 60, 60a, the second fluid (along with the first fluid) may flow past the valve element 8, 8a into and through the channel 88, 88a of the third port 62, 62a and into the second fluid transfer device 202, 202a. In one embodiment of FIGS. 1, fluid may pass through the channels 93 as the fluid flows between the second port 60 and the third port 62. Moreover, in the embodiment of FIGS. 2, fluid may flow past the valve element 8a and flow in between ribs 71a, around the circular flange 80a via path 91a, through fluid port 93a and out channel 88a. Alternatively, fluid may flow in the opposite direction when fluid is transferred from the second port 60, 60*a* to the third fluid transfer device 204, 204*a*.

If and when the third fluid transfer device 204, 204*a* is removed from the second port 60, 60*a*, the second valve element 8, 8*a* may return to its first position (e.g., with the top 67, 67*a* of the second valve element substantially flush with the top 73, 73*a*). In the embodiment of FIGS. 1, this may result in negative pressure (i.e., fluid within the connector 2, the first fluid transfer device 200, and/or the second fluid transfer device 202 may flow in a direction towards the opening portion 80).

In the embodiment of FIGS. 2, as the second valve element 8*a* moves to its first position, air may flow from outside the connector 2*a* through channels Ha and into chamber 77*a*. Such a construction may result in positive pressure or self-flushing (i.e., fluid within the connector 2*a*, the first fluid transfer device 200*a*, and/or the second fluid transfer device 202*a* may flow in a direction 206*a*). It should be understood that any self-flushing construction may be integrated into the connector 2, 2*a*, such as those constructions disclosed in U.S. Pat. No. 5,730,41S, which is incorporated herein by reference. In both FIGS. 1 and 2, negative pressure may also occur if and when the first fluid transfer device 200, 200*a* is removed from the first port 22.

In some embodiments, a needleless valve has collapsible internal valve made of a flexible material. When a force is applied to the top of the valve by the tip of a male Luer connector, the valve folds at a "smiley cut" located in the upper portion, referred to as the "head" of the valve, thereby opening a flow path through the connector. As the size of this type of connector is reduced, however, the behavior of the flexible valve may not scale and the valve having a single smiley cut may not fold at the desired amount of force.

Most needleless connectors trap some amount of fluid when the connector is disconnected from a previously mated connector. As some medical fluids degrade with time, this trapped fluid may present a hazard to a patient. A self-sealing needleless female Luer connector disclosed herein is reduced in size and, therefore, may trap a reduced amount of fluid within the connector upon disconnection. The disclosed connector also accepts a standard male Luer fitting and provides a self-sealing port with a continuous external surface at the port when the connector is not activated such that the port may be disinfected prior to use.

In some embodiments, a needleless connector is disclosed that includes a body having an internal cavity with a sealing ridge, a port, an output flow channel, and a fluid flow path between the port and output flow channel. The connector also includes a collapsible valve disposed within the cavity. The valve has a cylindrical wall having a center axis and a shoulder and defining an internal air space, wherein the shoulder is configured to sealingly contact the ridge of the body so as to block the fluid flow path, and a head fixedly attached to the wall. The head has first and second smiley cuts disposed on opposite sides of the head.

In some embodiments, a collapsible valve is disclosed that includes a cylindrical wall having a center axis and defining an internal air space and a head fixedly attached to the wall. The head can have first and second smiley cuts disposed on opposite sides of the head.

A needleless connector can have a shoulder that continuously contacts a ridge within the cavity when the connector is de-activated, i.e., not connected to a mating connector, to form a primary seal that blocks the fluid flow path through the connector. The valve has an internal air space that is separated from the cavity by a cylindrical wall. The air space is vented to the ambient environment through air passages and the external cavity within the threaded connector surrounding the male Luer fitting of the body, as indicated by the air flow path. The valve also has a solid head with a "smiley cut" formed on one side and a top surface that is positioned generally flush with a port of the cavity when the connector is de-activated. The edge of the top surface seals to the port. The top surface is continuous, i.e., there is no slit or penetration in the surface that may trap bacteria or other contamination. A connector can have a representative overall length. In certain valves, a representative overall length (L1) can be 1.324 inches.

In an activated position, i.e., a male Luer fitting sealingly coupled to the connector at the port, the tip of the male Luer fitting displaces an external surface downward and the applied force causes the head to buckle toward the smiley cut as well as causing the cylindrical wall to buckle. In the activated configuration, the primary seal between the shoulder and ridge is opened such that fluid may flow through the connector, passing from the lumen of the male Luer fitting through the cavity and through channels in the base and out through an output flow channel of the male fitting that is fluidly coupled to the flow channel of the connected female Luer fitting. Air passes out of the air chamber along the air flow path as the valve collapses.

In some aspects of the present disclosure, a needleless connector allows the connection and disconnection of a male Luer fitting, seals the flow path when there is no fitting mated with the connector, and contains the least possible amount of fluid in the needleless connector. To this end, the disclosed needleless connector 700 provides a smaller body that results in a smaller internal volume of fluid compared to a conventional connector. As a medication that remains trapped in the connector may not reach a patient, unless the connector is flushed with a medical liquid such as a saline solution, reducing the liquid volume of a needleless connector increases the amount of the medication that reaches the patient. In addition, as medications may degrade over time and connectors may not always be flushed after administration of the medication through a needleless connector, a reduction in the trapped volume of a medication in a connector necessarily reduces the amount of degraded medication that may reach the patient at a later time.

FIGS. 13A-13B are cross-sections of an exemplary needleless connector 400 according to certain aspects of the present disclosure. The connector 400 has a body 450 that defines a cavity 451. The connector 400 has a characteristic length (L2) that can be less than L1. In certain embodiments, L2 is less than 90% of L1. In certain embodiments, L2=1.200 inches. The smaller body 450 contains less fluid than a conventional connector. The port 452 and the male Luer fitting 439 of the connector 400 meet the same ISO standards as the port and fitting of a conventional connector. In certain embodiments, the male Luer fitting 439 may be replaced with a tubing connector (not shown) that accepts an end of a length of tubing, for example when a connector 400 is integrated into an IV set.

As the size of the connector 400 is reduced compared to a conventional connector, the volume of the cavity 451 that is external to the valve 420 is also reduced compared to a conventional connector. As the wall thickness of the body 450 and some internal features must remain the same as body of a conventional connector, for example to provide a minimum thickness for flow of molten plastic in a molding process, the reduction in the fluid volume may be proportionately greater than the reduction in a linear dimension. In certain embodiments, the reduction in fluid volume may be 40% while the reduction in the linear dimension L2 vs. L1 may be only 10%.

The connector 400 has a valve 420 disposed within the cavity 451 that is generally similar to the valve of a conventional connector. The valve 420 comprises a flexible material, for example silicone. Valve 420 has a center axis 401 and a head 422 with two smiley cuts 426, 428 disposed on opposite sides of the head. The details of the smiley cuts are discussed in greater detail in FIGS. 14-16.

Figure 14:
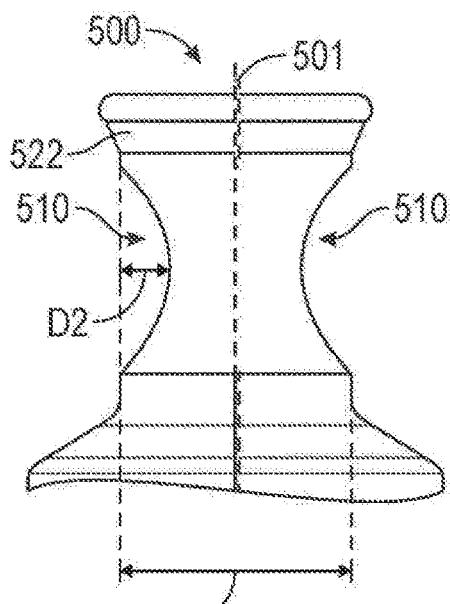
FIGS. 14-16 are side views of various example embodiments of the head of a valve according to certain aspects of the present disclosure.
Figure 15:
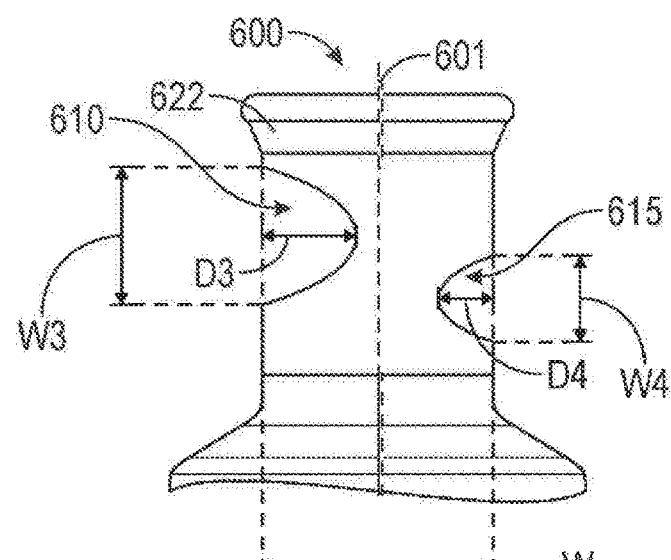
Figure 16:
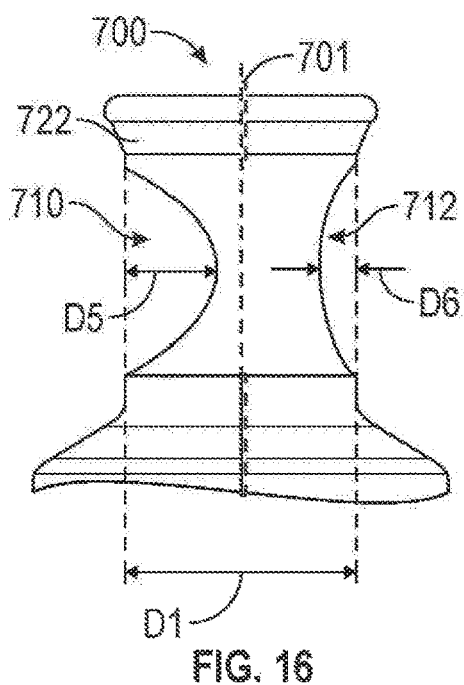

FIGS. 14-16 are cross-sections of various example embodiments of a valve according to certain aspects of the present disclosure. FIG. 14 depicts the head 522 of a valve 500 that is similar to valve 420 of FIGS. 13A-13B. The valve 500 has two identical smiley cuts 510 that are equally spaced from a center axis 501 of the valve 500 and have a common depth D2. The smiley cuts 510 have a uniform profile, i.e., the shape is the same over the length of the smiley cut, through the head 522. In FIG. 14, the directions of length, width, and depth of the smiley cuts are shown by the coordinate legend in FIG. 15, wherein the curved arrow indicates that length "L" is defined as directed into the plane of the drawing. The length of a smiley cut is defined as the value of the uniform profile in the direction of length L as measured at the maximum depth D. In certain embodiments, the depth D2 is defined at the center of the profile.

In certain embodiments, the profile is symmetric. In certain embodiments, the profile is not symmetric. In certain embodiments, first and second smiley cuts each have a uniform profile through the head. In certain embodiments, the profile has a constant radius. In certain embodiments, the profile has a variable radius. In certain embodiments, at least one of the profiles of a first and second smiley cuts comprises a variable radius. In certain embodiments, at least one of the profiles of a first and second smiley cuts comprises a parabola. In certain embodiments, D2 is less than or equal to 30% of a diameter D1 of the head 522. In certain embodiments, D2 is less than or equal to 25% of D1. In certain embodiments, D1=0.450 inches. In certain embodiments, D2=0.038 inches. In certain embodiments, a point of maximum depth of a second smiley cut is axially offset along the center axis from a point of maximum depth of a first smiley cut.

FIG. 15 depicts the head 622 of a valve 600 that is similar to valve 420 of FIGS. 13A-13B. The valve 600 has smiley cuts 610, 615 that are disposed on opposite sides of head 622 with depths D3, D4 respectively. In certain embodiments, D3 is equal to or greater than 30% of D1 while D4 is less than or equal to 25% of D1. In this example, smiley cut 615 is axially offset along the center axis 601 from smiley cut 610. In this example, the smiley cuts 610, 615 each have a parabolic profile, wherein the profile of smiley cut 610 is not the same profile as smiley cut 615. In certain embodiments, D3 and D4 are equal while smiley cuts 610, 615 have different parabolic profiles such that the respective widths W3, W4 of the smiley cuts 610, 615 are not equal. In certain embodiments W3 and W4 are equal.

FIG. 16 depicts the head 722 of a valve 700 that is similar to valve 420 of FIGS. 13A-13B. The valve 700 has smiley cuts 710, 712 that are disposed on opposite sides of head 722. In this example, smiley cuts 710, 712 are axially aligned with different depths D5, D6. In certain embodiments, D5 is equal to or greater than 50% of D1. In certain embodiments, D6 is less than or equal to 20% of D1. In this example, smiley cut 710 has a parabolic profile while smiley cut 712 has a constant radius profile.

It can be seen that the disclosed embodiments of the needleless connector have a reduced internal volume of fluid while providing a self-sealing connection port of the same size and configuration of a conventional needleless connector. This reduction in fluid volume reduces the amount of fluid that remains trapped in the disclosed needleless connector when a connector attached to an IV line or a container such as a syringe is disconnected from the connector. While some amount of fluid is unavoidably retained in any needleless connector, reducing the amount of fluid that remains trapped in a connector increases the amount of an administered medication that reaches the patient. In addition, as medications may degrade over time, a reduction in the trapped volume of a medication in a connector necessarily reduces the amount of degraded medication that may reach the patient at a later time.

Although the present invention and its advantages have been described in detail, it should be understood that various changes, substitutions and alterations can be made herein without departing from the spirit and scope of the invention as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, compositions of matter, means, methods, or steps, presently existing or later to be developed that perform substantially the same function or achieve substantially the same result as the corresponding embodiments described herein may be utilized according to the present invention. Accordingly, the appended claims are intended to include within their scope such processes, machines, manufacture, compositions of matter, means, methods, or steps.

What is claimed is:

1. A connector for transferring fluid, the connector comprising:
   a housing comprising a base having a first port, and a cap having a second port, the base and cap defining a channel that extends between the first and second ports; and
   a valve element comprising a body, a head, and a longitudinal axis between the body and the head, the body having a wall with an inner surface defining an internal chamber, and the head coupled to the body and having a first notch and a second notch, wherein the first and second notches are positioned on opposite surfaces of the head and define a reduced cross-sectional portion of the head between the first and second notches, and wherein the valve element is positioned within the channel with the head within the second port.

2. The connector of claim 1, wherein the body comprises a third notch.

3. The connector of claim 2, wherein a fourth notch and a fifth notch extend along an inner surface of the wall.

4. The connector of claim 3, wherein the fourth and fifth notches extend along opposite surfaces of the inner surface of the wall.

5. The connector of claim 3, wherein the fourth and fifth notches are axially offset along the longitudinal axis.

6. The connector of claim 1, wherein the first and second notches comprise a common width and a common depth.

7. The connector of claim 1, wherein the first and second notches have a depth that extends transverse to the longitudinal axis, and the first notch has a first depth and the second notch has a second depth that is less than the first depth.

8. The connector of claim 1, wherein the first and second notches have a width that extends along the longitudinal axis, and the first notch has a first width and the second notch has a second width that is less than the first width.

9. The connector of claim 1, wherein the first notch is longitudinally offset, relative to the second notch, along the longitudinal axis.

10. The connector of claim 1, wherein the reduced cross-sectional portion comprises a maximum thickness that is between thirty percent and fifty percent of a diameter of the head.

11. The connector of claim 1, wherein the base comprises a flange configured to be retained between the base and the cap to seal the internal chamber and separate the channel into an air chamber in fluid communication with an outside of the connector via a passage of the base, and a liquid chamber continuously coupled to the first port.

12. The connector of claim 1, wherein the valve element comprises a first position and a second position within the channel, the head configured to seal the second port when the valve element is in the first position.

13. A connector for transferring fluid, the connector comprising:
 a housing comprising a first port, a second port, and a channel that extends between the first and second ports; and
 a valve element positioned within the channel, the valve element comprising:
  a head having an outer surface comprising a first diameter, a first notch, and a second notch, and a reduced cross-sectional portion defining a thickness between the first and second notches, wherein the first and second notches are positioned on opposite surfaces of the head;
 a body coupled to the head, the body having a wall with an outer surface defining a second diameter, and an inner surface defining an internal chamber; and
 a longitudinal axis extending between the body and the head, wherein the thickness between the first and second notches is less than the first and second diameters.

14. The connector of claim 13, wherein the inner surface of the body comprises a third notch.

15. The connector of claim 14, wherein the third notch is axially offset along the longitudinal axis, relative to any of the first and second notches.

16. The connector of claim 13, wherein the first and second notches have a depth that extends transverse to the longitudinal axis, and the first notch has a first depth and the second notch has a second depth that is less than the first depth.

17. The connector of claim 13, wherein at least one profile of the first and second notches comprises a constant radius.

18. The connector of claim 13, wherein the first notch is longitudinally offset, relative to the second notch, along the longitudinal axis.

19. The connector of claim 13, wherein the thickness of the reduced cross-sectional portion is between thirty percent and fifty percent of the first diameter.

20. The connector of claim 13, wherein the valve element comprises a first position and a second position within the channel, the head configured to seal the second port when the valve element is in the first position.

* * * * *